(12) United States Patent
Kim et al.

(10) Patent No.: US 12,097,356 B2
(45) Date of Patent: Sep. 24, 2024

(54) LIQUID MEDICINE INJECTION DEVICE

(71) Applicant: EOFLOW CO., LTD., Seongnam-si (KR)

(72) Inventors: Seungha Kim, Goyang-si (KR); Hyunduk Roh, Seoul (KR); Seonhwan Kim, Seongnam-si (KR); Daejong Park, Seoul (KR)

(73) Assignee: EOFLOW CO., LTD., Seongnam-si (KR)

( * ) Notice: Subject to any disclaimer, the term of this patent is extended or adjusted under 35 U.S.C. 154(b) by 0 days.

(21) Appl. No.: 18/426,297

(22) Filed: Jan. 29, 2024

(65) Prior Publication Data

US 2024/0165331 A1 May 23, 2024

Related U.S. Application Data

(63) Continuation of application No. 18/116,962, filed on Mar. 3, 2023, now Pat. No. 11,918,784, which is a
(Continued)

(30) Foreign Application Priority Data

Sep. 7, 2020 (KR) ........................ 10-2020-0114111
Oct. 15, 2020 (KR) ........................ 10-2020-0133191

(51) Int. Cl.
*A61M 5/178* (2006.01)
*A61M 5/32* (2006.01)

(52) U.S. Cl.
CPC ............... *A61M 5/178* (2013.01); *A61M 5/32* (2013.01)

(58) Field of Classification Search
CPC .......... A61M 5/16831; A61M 5/31568; A61M 5/14248; A61M 5/31593; A61M 5/1684; A61M 5/14566; A61M 5/20; A61M 5/31541; A61M 5/31585; A61M 5/31553; A61M 5/14216; A61M 5/31596; A61M 5/007; A61M 5/145; A61M 5/158; A61M 5/48; A61M 5/46; A61M 5/31578; A61M 5/31543; A61M 5/24; A61M 5/31583; A61M 5/14276; A61M 5/1456; A61M 5/14212; A61M 5/1723; A61M 5/178; A61M 2205/3306; A61M 2205/502;
(Continued)

(56) References Cited

U.S. PATENT DOCUMENTS

2004/0092878 A1 5/2004 Flaherty
2007/0073229 A1 3/2007 Gorman et al.
2017/0128664 A1 5/2017 Diianni et al.

FOREIGN PATENT DOCUMENTS

JP 2003247857 9/2003
JP 2020-527424 9/2020
KR 1020200086707 7/2020

OTHER PUBLICATIONS

Non-Final Office Action dated Jul. 8, 2022, issued in Korean Patent Application No. 10-2020-0114111.
(Continued)

*Primary Examiner* — Manuel A Mendez
(74) *Attorney, Agent, or Firm* — PnK IP LLC

(57) ABSTRACT

A medical liquid injection device includes a base body, a needle assembly mounted on the base body, a reservoir fluidly connected to the needle assembly and having a plunger therein, a driving unit that linearly moves the plunger, and an encoder unit disposed at an end of the driving unit to measure rotation of the driving unit.

2 Claims, 17 Drawing Sheets

Related U.S. Application Data continuation of application No. PCT/KR2021/012116, filed on Sep. 7, 2021.

(58) Field of Classification Search
CPC ........ A61M 2205/52; A61M 2205/332; A61M 2205/3365; A61M 2205/3327; A61M 2205/581; A61M 2205/583; A61M 2205/15; A61M 2205/3126; A61M 2205/16863; A61M 2205/14252; A61M 2205/2407; A61M 2205/14284; F04B 19/22; B01L 2300/0663; G06F 19/3468

See application file for complete search history.

(56) References Cited

OTHER PUBLICATIONS

Final Office Action dated Mar. 6, 2023, issued in Korean Patent Application No. 10-2020-0114111.
Notice of Allowance dated Jun. 28, 2023, issued in Korean Patent Application No. 10-2020-0114111.
Notice of Non-Final Rejection dated Jul. 25, 2022, issued in Korean Patent Application No. 10-2020-0133191.
Notice of Allowance dated Sep. 26, 2022, issued in Korean Patent Application No. 10-2020-0133191.

LIQUID MEDICINE INJECTION DEVICE

CROSS-REFERENCE TO RELATED APPLICATIONS

This application is a Continuation Application of U.S. application Ser. No. 18/116,962, filed on Mar. 3, 2023, which is a Continuation Application of International Patent Application No. PCT/KR2021/012116, filed on Sep. 7, 2021, which claims priority to Korean Patent Application No. 10-2020-0114111, filed on Sep. 7, 2020 and Korean Patent Application No. 10-2020-0133191, filed on Oct. 15, 2020, each of which is hereby incorporated by reference for all purposes as if fully set forth herein.

BACKGROUND

Field

The present disclosure relates to a medical liquid injection device. The present disclosure also provides a method, device and computer program product for determining over-injection or under-injection of a medical liquid.

Discussion of the Background

Diabetes is a metabolic disorder that causes signs that blood glucose is outside a normal range due to an insufficient secretion or malfunction of insulin. Diabetes is a complex disease that have a potential to affect each tissue of human body due to complications such as blindness, renal failure, heart failure and neuropathy may affect various tissues of the human body, and the number of diabetic patients is said to increase every year.

In the case of diabetes, it is necessary to measure blood glucose using a blood glucose meter and manage blood glucose through appropriate means such as diet, exercise program, insulin injection, oral diabetes medicine, and the like.

Recently, a technology for more accurately determining whether a medical liquid is over-injected or under-injected is required.

SUMMARY

An object of the present disclosure is to provide a medical liquid injection device that is safely operated and may accurately deliver a medical liquid. In addition, an object of the present disclosure is to provide a method, a device and a computer program product for determining over-injection or under-injection of the medical liquid. The technical problem to be achieved by the present embodiment is not limited to the technical problems described above, and other technical problems may be inferred from the following embodiments.

One aspect of the present disclosure provides a medical liquid injection device including a base body, a needle assembly mounted on the base body, a reservoir fluidly connected to the needle assembly and having a plunger therein, a driving unit that linearly moves the plunger, and an encoder unit disposed at an end of the driving unit to measure rotation of the driving unit.

A medical liquid injection device according to an embodiment of the present disclosure may check whether the device is normally operated and may measure an injection amount of medical liquid stored in a reservoir. The encoder unit may accurately measure data on rotation of a driving wheel and sense whether the medical liquid injection device is normally driven. In addition, since the encoder unit measures a rotation angle of the driving wheel and calculates a moving distance of a plunger, an amount of medical liquid injected into a user from the medical liquid injection device may be measured.

In the medical liquid injection device according to an embodiment of the present disclosure, the encoder unit may accurately sense the rotation of the driving wheel. Since a step is disposed between the driving wheel and a tooth end, the encoder unit is accurately electrically connected or electrically shorted by the step. The encoder unit may accurately measure the electrical connection/short, so that the rotation angle of the driving wheel may be accurately measured and the injection amount of the medical liquid may be accurately measured.

The medical liquid injection device according to an embodiment of present disclosure may reduce a control load by using data measured by the encoder unit. By calculating the rotation angle of the driving wheel based on ON/OFF signal measured by the encoder unit, it is possible to quickly calculate the rotation angle of the driving wheel, the moving distance of the plunger and the injection amount of the medical liquid. Of course, the scope of the present disclosure is not limited by these effects.

According to the above-described problem solving means of the present disclosure, the over-injection or under-injection may be determined more accurately by determining the over-injection or under-injection of the medical liquid based on number of confirmations of the contact pattern before changing for the encoder unit.

In addition, the number of confirmations of the contact pattern before changing is accumulated and stored in a buffer until number of changes of the contact pattern is equal to or greater than a preset number, and the over-injection or under-injection of the medical liquid is determined based on an accumulated number of confirmations stored in the buffer, so that the over-injection or under-injection may be determined more accurately.

DETAILED DESCRIPTION

Figure 1:
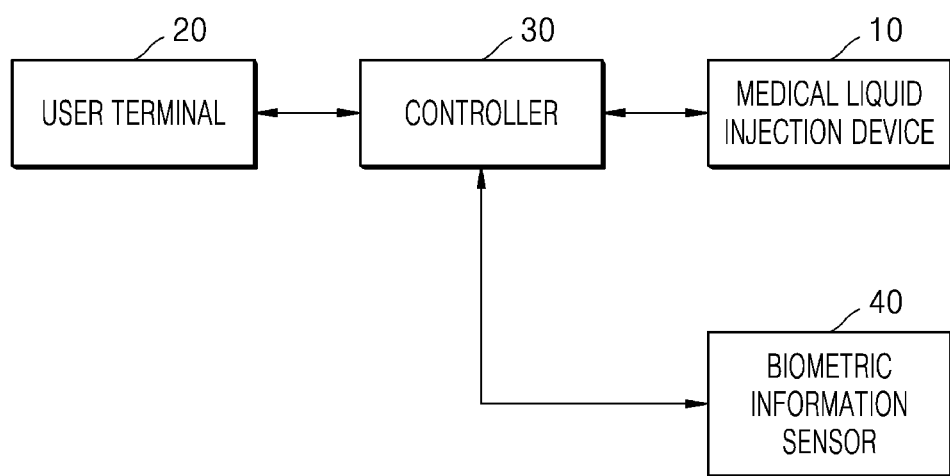
FIG. 1 is a block diagram illustrating a medical liquid injection system according to an embodiment of the present disclosure.

As a technical means for achieving the above-described technical problem, one aspect of the present disclosure provides a medical liquid injection device including a base body, a needle assembly mounted on the base body, a reservoir fluidly connected to the needle assembly and having a plunger therein, a driving unit that linearly moves the plunger, and an encoder unit disposed at an end of the driving unit to measure rotation of the driving unit.

In addition, the encoder unit may include a base cover mounted on the end of the driving unit and rotating together with the driving unit, a first contact end connected to contact one side of the base cover, and a second contact end disposed on the other side of the base cover and selectively contacting the base cover according to rotation of the driving unit.

In addition, the base cover may include a cover end extending in a circumferential direction of the rotating driving unit, and a plurality of tooth ends extending from the cover end and spaced apart from each other along a circumferential direction of the cover end.

In addition, the driving unit may include a protruding end disposed between the adjacent tooth ends, and the protruding end and the tooth end have a step in a circumferential direction.

In addition, the first contact end and the second contact end may have elasticity.

Another aspect of the present disclosure may be providing a medical liquid injection device including a base body, a needle assembly mounted on the base body, a reservoir fluidly connected to the needle assembly and having a plunger therein, a driving unit that linearly moves the plunger, an encoder unit disposed at an end of the driving unit to measure rotation of the driving unit, and a control module determining over-injection or under-injection of a medical liquid based on the detection of the rotation of the driving unit by the encoder unit.

Another aspect of the present disclosure may provide a method for determining over-injection or under-injection of a medical liquid, wherein the method includes determining that a current contact pattern for an encoder unit is a first contact pattern based on sensing rotation of a driving unit by the encoder unit; calculating a number of confirmations by checking whether the current contact pattern is maintained as the first contact pattern; obtaining the number of confirmations of the first contact pattern in response to a change of the current contact pattern from the first contact pattern to a second contact pattern; and determining whether the medical liquid is over-injected or under-injected based on the number of confirmations.

Another aspect of the present disclosure may provide a computer program product including one or more computer-readable recording media on which a program to perform determining that a current contact pattern for an encoder unit is a first contact pattern based on sensing rotation of a driving unit by the encoder unit; calculating a number of confirmations by checking whether the current contact pattern is maintained as the first contact pattern; obtaining the number of confirmations of the first contact pattern in response to a change of the current contact pattern from the first contact pattern to a second contact pattern; and determining whether the medical liquid is over-injected or under-injected based on the number of confirmations is stored.

Hereinafter, with reference to the accompanying drawings, an embodiment of the present disclosure will be described in detail so that a person having ordinary knowledge in the technical field to which the present disclosure belongs may easily practice it. However, present disclosure may be implemented in many different forms and is not limited to the embodiments described herein. And in order to clearly explain the present disclosure in the drawings, parts irrelevant to the description are omitted, and similar reference numerals are attached to similar parts throughout the specification.

Throughout the specification, when a part is said to be connected to another part, this includes not only the case where it is directly connected but also the case where it is electrically connected with another element interposed therebetween. In addition, when a part includes a certain component, this means that it may further include other components without excluding other components unless otherwise stated.

Hereinafter, the present disclosure will be described in detail with reference to the accompanying drawings.

FIG. 1 is a block diagram illustrating a medical liquid injection system 1 according to an embodiment of the present disclosure.

Referring to FIG. 1, a medical liquid injection system 1 may include a medical liquid injection device 10, a user terminal 20, a controller 30 and a biometric information sensor 40. In the medical liquid injection system 1, a user may drive and control the system by using the user terminal 20, and the medical liquid injection device 10 may periodically inject medical liquids based on blood glucose information monitored by the biometric information sensor 40.

The medical liquid injection device 10 injects medical liquids, such as insulin, glucagon, anesthetics, painkillers, dopamine, growth hormone, and smoking cessation aids to be injected into the user based on the data sensed by the biometric information sensor 40.

In addition, the medical liquid injection device 10 may transmit a device status message including remaining battery capacity information of the device, whether the device boots successfully, whether injection is successful, etc. to the controller 30. Messages transmitted to the controller may be transmitted to the user terminal 20 via the controller 30. Alternatively, the controller 30 may transfer improved data obtained by processing received messages to the user terminal 20.

In one embodiment, the medical liquid injection device 10 is provided separately from the biometric information sensor 40 and may be installed apart from an object. In another embodiment, the medical liquid injection device 10 and the biometric information sensor 40 may be provided in one device.

In one embodiment, the medical liquid injection device 10 may be mounted on a user's body. In another embodiment, the medical liquid injection device 10 may be mounted on an animal to inject a medical liquid.

The user terminal 20 may receive an input signal from the user to drive and control the medical liquid injection system 1. The user terminal 20 may generate a signal driving the controller 30 and control the controller 30 to drive the medical liquid injection device 10. In addition, the user terminal 20 may display biometric information measured from the biometric information sensor 40 and may display state information of the medical liquid injection device 10.

The user terminal 20 refers to a communication terminal usable in a wired/wireless communication environment. For example, the user terminal 20 may be a smart phone, tablet PC, PC, smart TV, mobile phone, personal digital assistant (PDA), laptop, media player, micro server, global positioning system (GPS) device, e-book reader, digital broadcasting terminal, navigation, kiosk, MP3 player, digital camera, consumer electronic, device with a camera, and other mobile or non-mobile computing device. In addition, the user terminal 2 may be a wearable device having a communication function and data processing function, such as a watch, glasses, a hair band, and a ring. However, as described above, a terminal equipped with an application capable of internet communication may be borrowed without limitation.

The user terminal 20 may be connected one-to-one with the pre-registered controller 30. The user terminal 20 may be encrypted and connected to the controller 30 in order to prevent the controller 30 from being driven and controlled by an external device.

In one embodiment, the user terminal 20 and the controller 30 may be separated and provided as separate devices. For example, the controller 30 may be provided to a subject equipped with the medical liquid injection device 10, and the user terminal 20 may be provided to the subject or a third party. The safety of the medical liquid injection system 1 may be increased by driving the user terminal 20 by a guardian.

In another embodiment, the user terminal 20 and the controller 30 may be provided as one device. The controller 30 provided as one with the user terminal 20 communicates with the medical liquid injection device 10 to control medical liquid injection.

The controller 30 transmits and receives data to and from the medical liquid injection device 10, transmits control signals related to injection of medical liquids such as insulin to the medical liquid injection device 10, and may receive control signals related to measurement of biological values such as blood glucose from the biometric information sensor 40.

For example, the controller 30 may transmit an instruction request to measure the user's current state to the medical liquid injection device 10 and receive measurement data from the medical liquid injection device 10 in response to the instruction request.

The biometric information sensor 40 may measure biological values such as blood glucose level, blood pressure, and heart rate of the user according to the purpose. Data measured by the biometric information sensor 40 may be transmitted to the controller 30, and a medical liquid cycle and/or injection amount may be set based on the measured data. Data measured by the biometric information sensor 40 may be transmitted to the user terminal 20 and displayed.

For example, the biometric information sensor 40 may be a sensor for measuring the amount of blood glucose of the object. The biometric information sensor may be a continuous glucose monitoring (CGM) sensor. The continuous glucose monitoring sensor is attached to the object and may continuously monitor the amount of blood glucose.

The user terminal 20, controller 30, and medical liquid injection device 10 may perform communication by using a network. For example, the network may include a local area network (LAN), a wide area network (WAN), a value added network (VAN), a mobile radio communication network, a satellite communication network, and these mutual combinations, may be a data communication network in a comprehensive sense that enables each network component to communicate smoothly with each other, and may include wired internet, wireless internet and mobile wireless communication network. In addition, wireless communication includes, for example, Wi-Fi, Bluetooth, Bluetooth low energy, Zigbee, Wi-Fi Direct (WFD), ultra wideband (UWB), infrared Data Association (IrDA), Near Field Communication (NFC), 5G, etc. may exist, but are not limited thereto.

Figure 2:
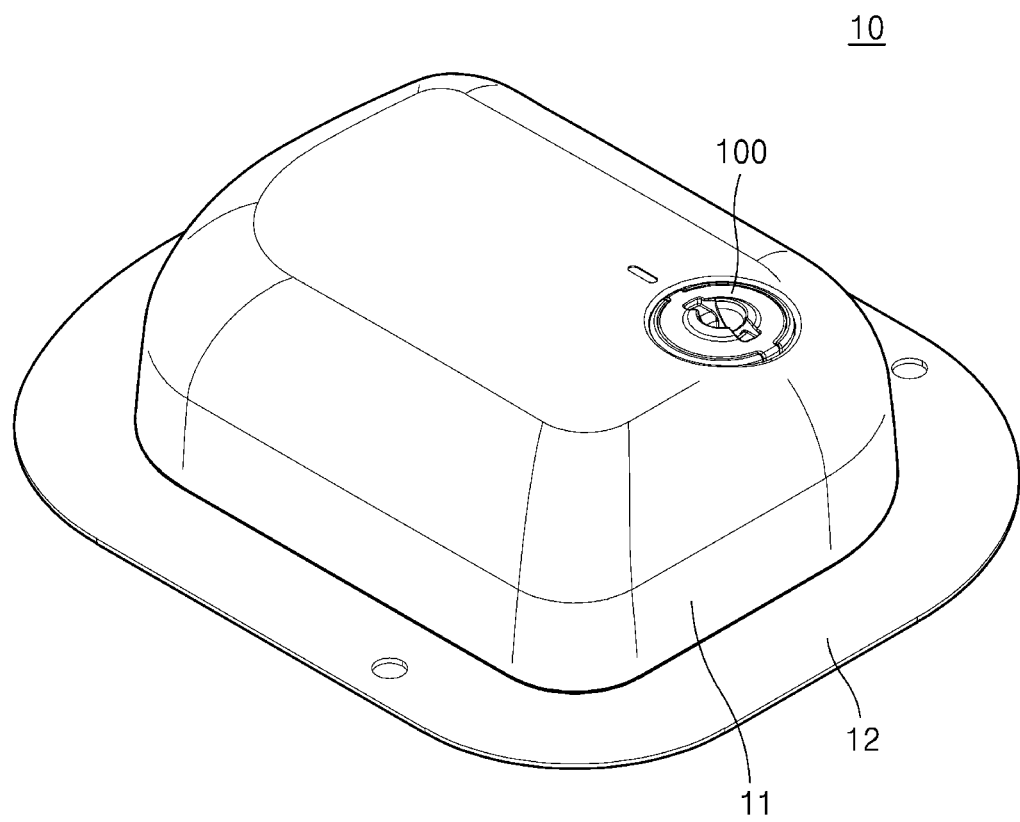
FIG. 2 is a perspective view illustrating a medical liquid injection device according to an embodiment of the present disclosure.
Figure 3:
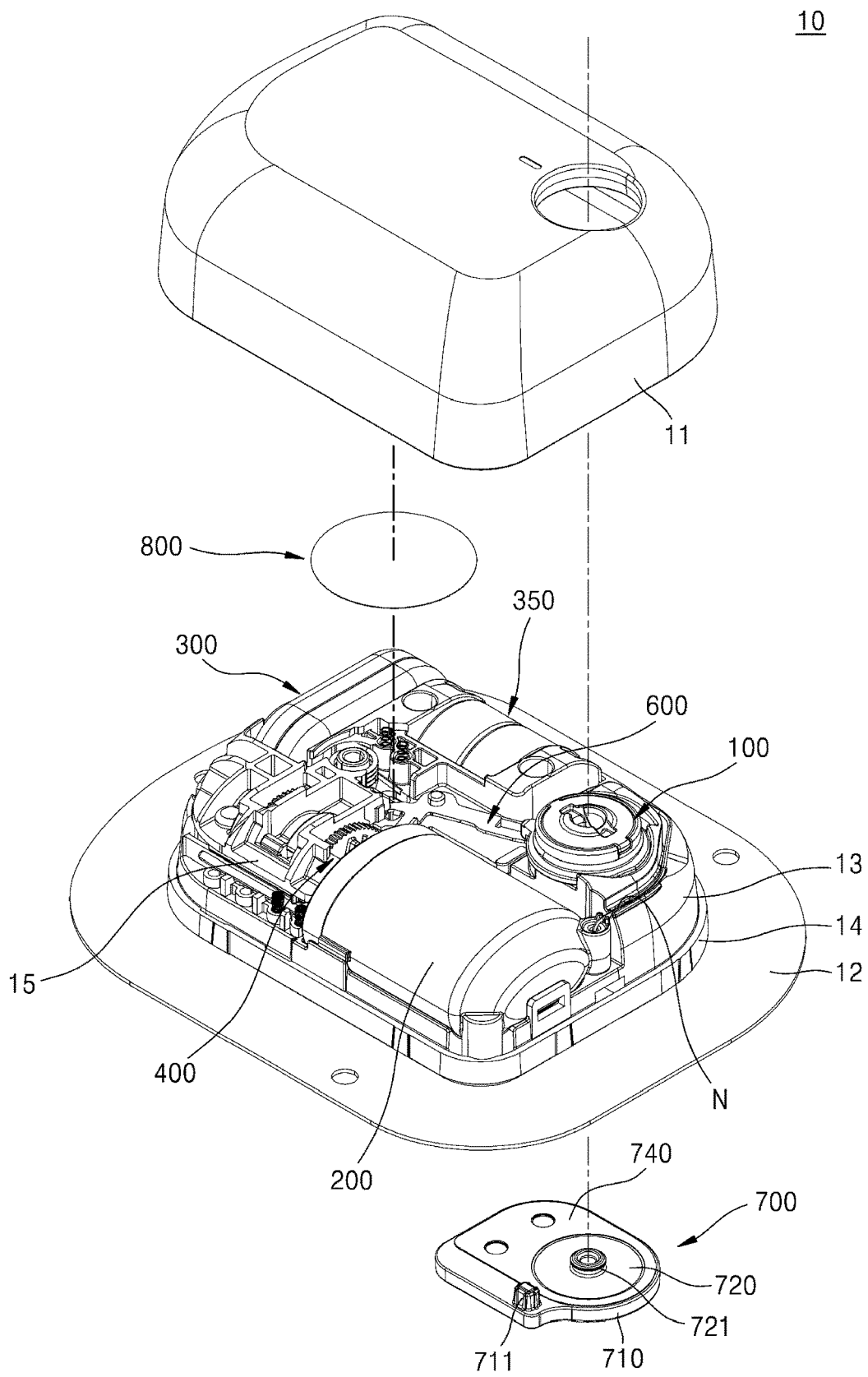
FIG. 3 is an exploded perspective view of the medical liquid injection device of FIG. 2.
Figure 4:
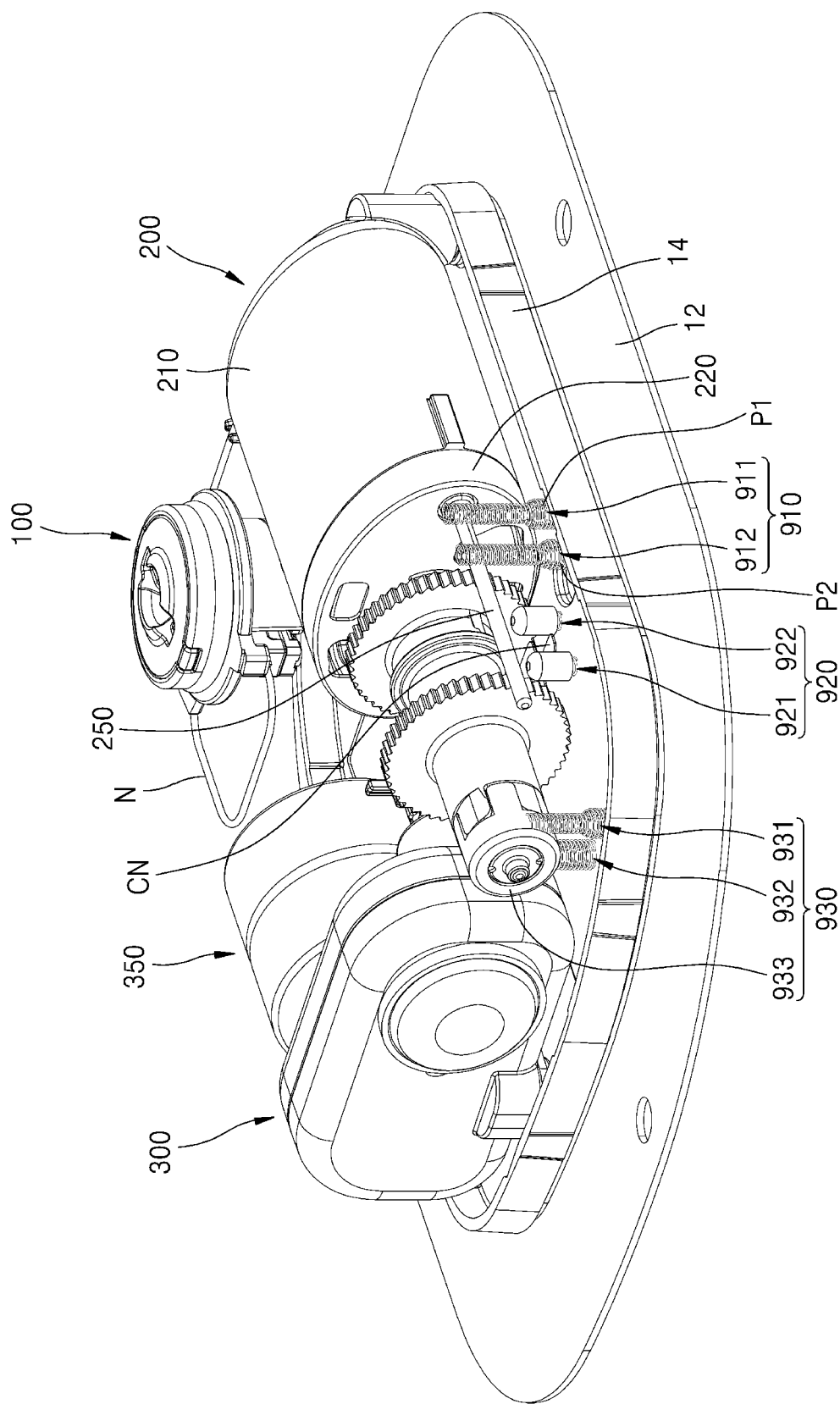
FIG. 4 is a perspective view illustrating some configurations of FIG. 3.
Figure 5:
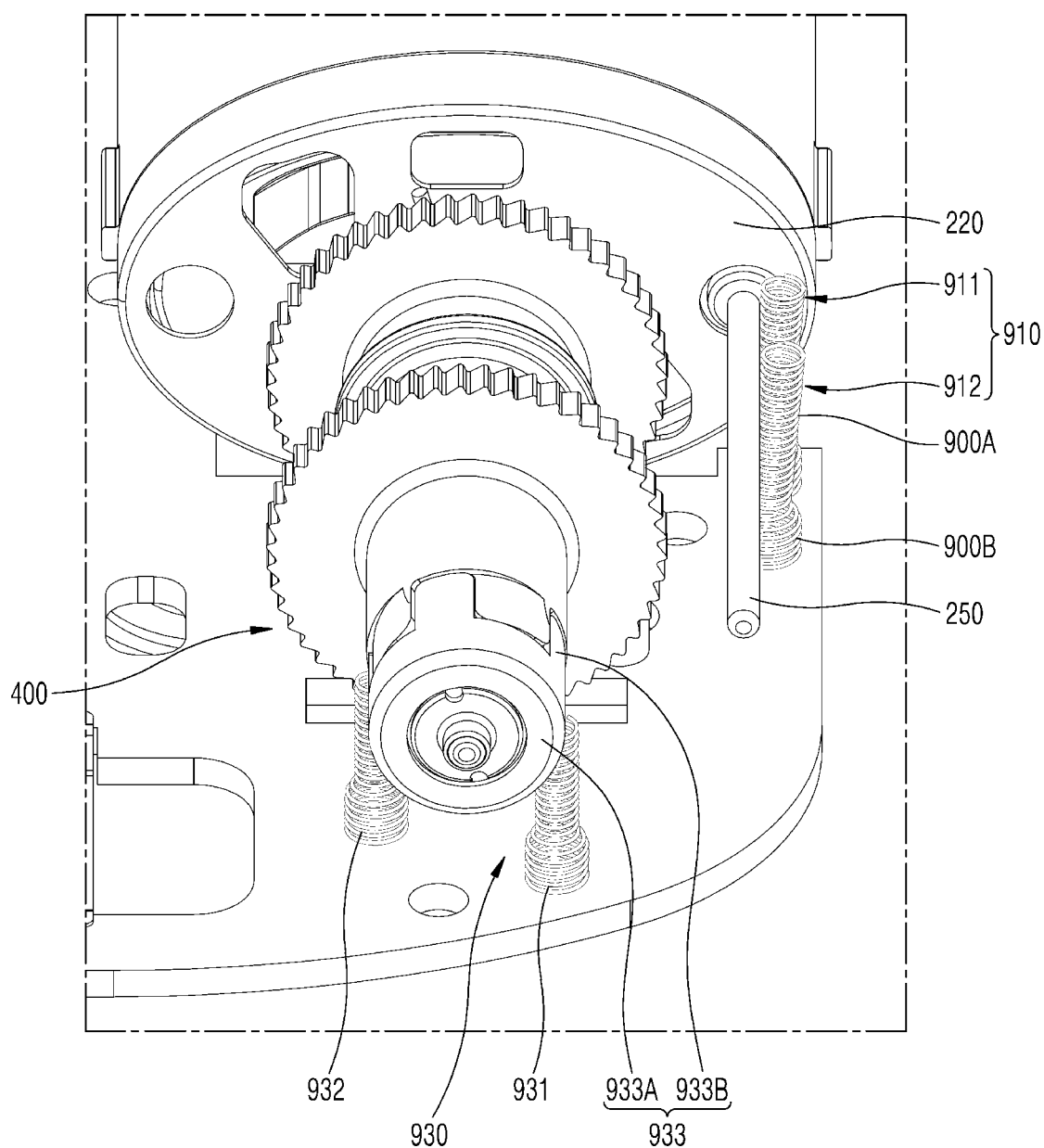
FIG. 5 is a perspective view illustrating one side of FIG. 4.

FIG. 2 is a perspective view illustrating a medical liquid injection device 10 according to an embodiment of the present disclosure, FIG. 3 is an exploded perspective view of the medical liquid injection device 10 of FIG. 2, FIG. 4 is a perspective view illustrating some configurations of FIG. 3, and FIG. 5 is a perspective view illustrating one side of FIG. 4.

Referring to FIGS. 2 to 5, the medical liquid injection device 10 is attached to a user to inject a medical liquid, and may inject the medical liquid stored therein in a set amount to the user.

The medical liquid injection device 10 may be used for various purposes depending on the type of medical liquid to be injected. For example, the medical liquid may include insulin-based medical liquids for diabetics, other pancreas medical liquids, heart medical liquids, and other various types of medical liquids.

One embodiment of the medical liquid injection device 10 may include a housing 11 covering an outside and an attachment part 12 positioned adjacent to the user's skin. The medical liquid injection device 10 includes a plurality of parts disposed in an inner space between the housing 11 and the attachment part 12. A separate bonding unit may be further disposed between the attachment part 12 and the user's skin, and the medical liquid injection device 10 may be fixed to the skin by the bonding unit.

The medical liquid injection device 10 may include a needle assembly 100, a reservoir unit 200, a driving module 300, a battery 350, a driving unit 400, a clutch unit 500, a trigger member 600, a needle cover assembly 700, an alarm unit 800 and a plurality of sensor units.

In the medical liquid injection device 10, the base body may form a frame in which at least one body supports internal parts. The base body may have a first body 13, a second body 14, and a third body 15 according to the arrangement.

The first body 13 is disposed under the housing 11, and the needle assembly 100, the reservoir unit 200, the driving module 300, the battery 350, etc. may be supported in each opening or groove. The second body 14 is disposed below the first body 13 and may be connected to the attachment part 12. The second body 14 may cover a lower portion of the medical liquid injection device 10. The third body 15 may be disposed above the first body 13, and the reservoir unit 200, the driving module 300, the battery 350, the driving unit 400, etc. may be supported in each opening or groove. In the drawing, the first body 13, the second body 14, and the third body 15 are illustrated, but are not limited thereto and may be integrally provided or provided in plurality.

A control module 16 may be disposed inside the medical liquid injection device 10. A control module 16, which is a circuit board, is disposed below the second body 14, and the control module may control the overall operation of the medical liquid injection device 10. The control module 16 is electrically connected to the driving module 300, the battery 350, the alarm unit 800 and a plurality of sensor units to control their driving.

The needle assembly 100 may be mounted on the first body 13. In the needle assembly 100, a needle N and/or a cannula may move in an axial direction by rotation of a sleeve 110.

One end of the needle N is connected to the reservoir unit 200 so that the medical liquid may be delivered, and the other end is inserted into the cannula and moved along the cannula.

Since the cannula has a conduit shape that may accommodate the needle N, the medical liquid discharged from the needle N may be injected into the user.

The cannula remains inserted into the user's skin, but the needle N rises and separates from the object. However, the cannula and the needle N form a path through which fluid moves, so that the medical liquid injected from the reservoir 210 may be injected into the user through the needle N and the cannula.

In the medical liquid injection device 10, the user may simply rotate the needle assembly 100, insert the cannula into the object, and start medical liquid injection.

The reservoir unit 200 is mounted on the first body 13 and the third body 15 and is connected to the needle assembly 100. In the reservoir unit 200, medical liquid D is stored in an inner space, and a fixed amount of medical liquid may be moved to the needle N according to the movement of a plunger. The reservoir unit 200 may include a reservoir 210, a cap cover 220, a plunger 230, a sealing ring 240 and a connector member 250 (see FIG. 6).

The reservoir 210 is extended to a preset length in a longitudinal direction, and may store the medical liquid in the inner space. The reservoir 210 may discharge the medical liquid through the needle N by moving the plunger 230. The cap cover 220 is mounted at an end of the reservoir 210, and a rod 410 and/or a connecting member 520 may move through an opening (not illustrated) disposed in the cap cover 220 (see FIG. 10).

The reservoir 210 may have an inlet end and an outlet end. The medical liquid is injected into the inlet end, the needle N is installed at the outlet end, and the medical liquid may be discharged through the needle N.

The plunger 230 is disposed inside the reservoir 210 and may linearly move by driving the driving module 300 and the driving unit 400. As the plunger 230 advances, the medical liquid may be discharged from the inner space to the needle N.

The plunger 230 may have an end 231 and an inclined surface 232. The end 231 may move toward a front 210F of the reservoir 210 to move the medical liquid. The inclined surface 232 may be closely attached to an inclined part of the reservoir 210.

The plunger 230 may be connected to a connector member 250 extending rearward. The connector member 250 may be installed on the plunger 230 and move linearly along with the linear movement of the plunger 230.

The connector member 250 is made of an electrically conductive material and may have a shaft shape. As the connector member 250 moves and contacts a first sensor unit 910, the storage amount of the medical liquid may be measured or the medical liquid injection device 10 may be started to operate.

The connector member 250 may be installed on a rear end of the plunger 230 and move along with the movement of the plunger 230. In the drawings, the connector member 250 is illustrated to have the shaft shape, but is not limited thereto and may have various shapes that generate electrical signals by contacting the first sensor unit 910.

When the medical liquid is stored in the reservoir 210 and the plunger 230 retracts, the connector member 250 may retract together with the plunger 230. In addition, when the plunger 230 advances so that the medical liquid is discharged from the reservoir 210 to the needle N, the connector member 250 may advance together with the plunger 230.

A sealing ring 240 is provided at a portion of the plunger 230 in contact with an inner wall of the reservoir 210 to prevent leakage of the medical liquid when the plunger 230 moves.

The driving module 300 may generate driving force and transmit the driving force to the driving unit 400. The driving force transmitted by the driving unit 400 linearly moves the plunger 230 inside the reservoir 210 to discharge the medical liquid.

When the driving units 400 are engaged with each other by the clutch unit 500, the driving module 300 rotates a driving wheel 420 of the driving unit 400, and the rotation of the driving wheel 420 moves a rod 410 linearly so that the plunger 230 may move. When the plunger 230 moves, the connector member 250 may also linearly move.

The driving module 300 may be used with all types of devices having medical liquid suction power and medical liquid discharge power by electricity. For example, all kinds of pumps such as mechanical displacement type micropumps and electromagnetic motion type micropumps may be used. The mechanical displacement type micropump is a pump that uses the motion of a solid or fluid, such as a gear or diaphragm, to generate a pressure difference to induce the flow of fluid, and includes a diaphragm displacement pump, a fluid displacement pump, a rotary pump, and the like. The electromagnetic motion type micropump is a pump that directly uses electrical or magnetic energy to move a fluid, and includes an electro hydrodynamic pump (EHD), an electro osmotic pump, a magneto hydrodynamic pump, an electro wetting pump, and the like.

The battery 350 may supply electricity to the medical liquid injection device 10 to activate each part. In the drawing, a pair of batteries 350 are illustrated, but are not limited thereto, and may be set in various ways according to the capacity, use range, and use time of the medical liquid injection device 10.

The battery 350 is disposed adjacent to the driving unit 400 and may supply electricity to the driving unit 400. In addition, the battery 350 is connected to the control module 16, and the sensor unit may measure data on the number of rotations or rotational speed of the driving unit 400, the amount of medical liquid stored in the reservoir 210, amount of medical liquid injected to the user, etc. based on the measured electrical signal.

Figure 10:
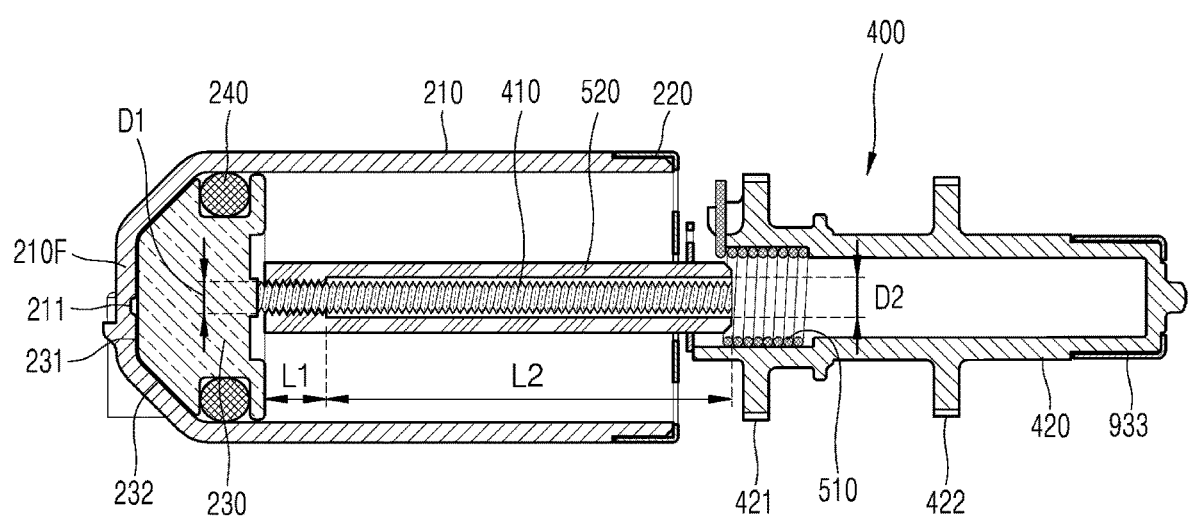
FIGS. 10 to 13 are cross-sectional views illustrating an operation of injecting a medical liquid into the reservoir, storing the medical liquid, and discharging the medical liquid through a needle.

Referring to FIG. 10, the driving unit 400 may be installed between the driving module 300 and the reservoir unit 200 to move the plunger 230 disposed in the reservoir 210 with the driving force generated by the driving module 300. However, the driving unit 400 may move the plunger 230 forward only when the rod 410 and the driving wheel 420 are coupled or connected by the clutch unit 500.

The rod 410 is connected to the plunger 230 and extends in one direction. The rod 410 is inserted into the opening of the cap cover 220, and the rod 410 may move in the longitudinal direction of the reservoir 210 to move the plunger 230. The rod 410 may have a threaded shape on the surface. The rod 410 is inserted into the connecting member 520 and is connected to the driving wheel 420 by the clutch unit 500 when the medical liquid is discharged in a fixed amount, so that the rod 410 may be moved to the front.

The driving wheel 420 is drivingly connected to the driving module 300 and may rotate by driving the driving module 300. The driving wheel 420 has a first connection end 421 and a second connection end 422, and may have a space in which the rod 410 may move. Since at least one of the first connection end 421 and the second connection end 422 is always operatively connected to the driving module 300 by a connector CN, the driving wheel 420 may rotate by driving the driving module 300.

In one embodiment, the first connection end 421 and the second connection end 422 may have a gear tooth shape. The connector CN connected to the driving module 300 applies gear teeth so that the driving wheel 420 may rotate.

In detail, the connector CN rotates repeatedly based on a rotational axis according to the linear reciprocating motion of the driving module 300. An end of the connector CN may rotate the driving wheel 420 by applying pressure to at least one of the first connection end 421 and the second connection end 422. For example, one end of the connector CN may be disposed to apply the first connection end 421, and the other end of the connector CN may be disposed to apply the second connection end 422.

When the connector CN rotates around the rotational axis, a second sensor unit 920 may measure the driving of the connector CN. The second sensor unit 920 may measure whether the driving force of the driving module 300 is transmitted to the driving wheel 420 by measuring whether it is in contact with the connector CN. In addition, the second sensor unit 920 may measure a rotated angle of the driving wheel 420 by measuring whether it is in contact with the connector CN.

The clutch unit 500 may drivingly connect the driving module 300 and the driving unit 400 to each other. The clutch unit 500 is disposed between the rod 410 and the driving wheel 420, and may include a coupler 510 and a connecting member 520.

Figure 11:
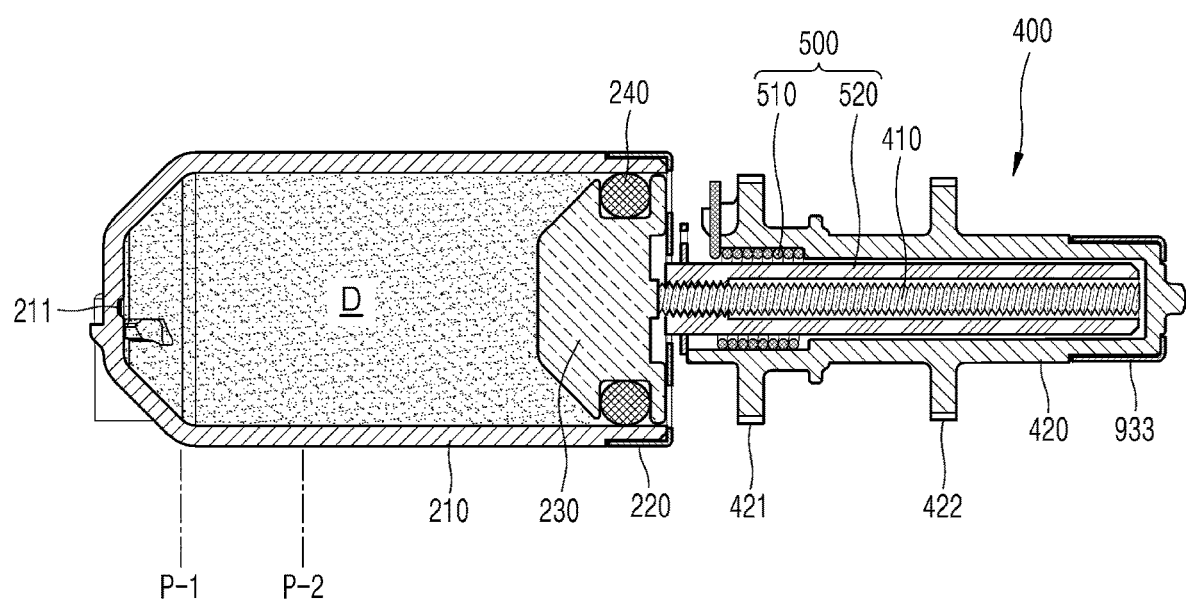
Figure 12:
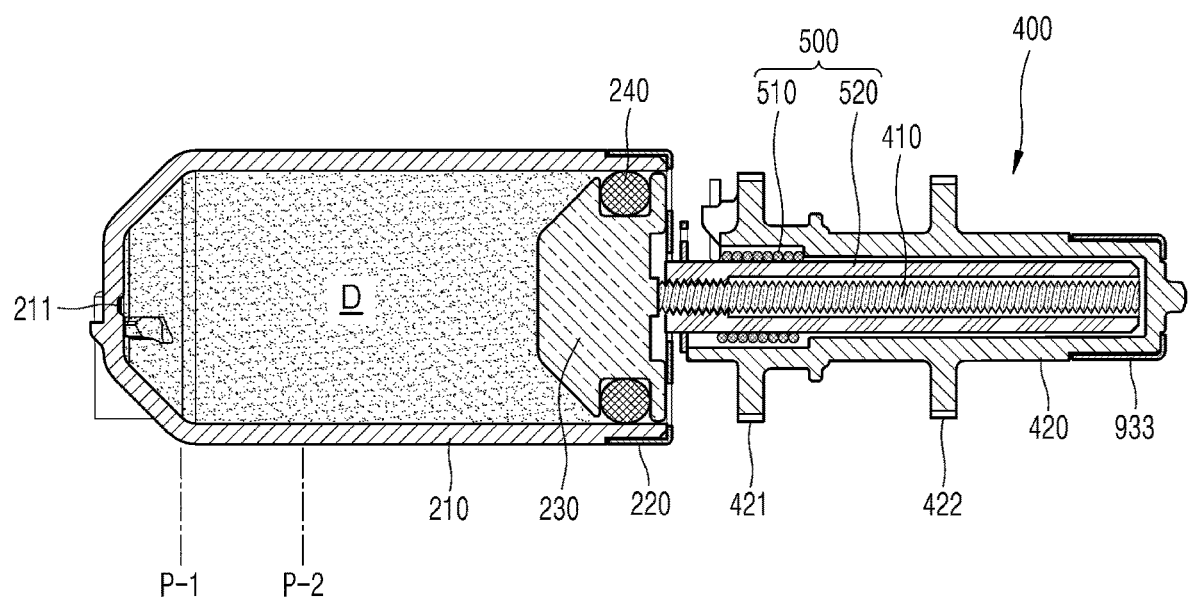
Figure 13:
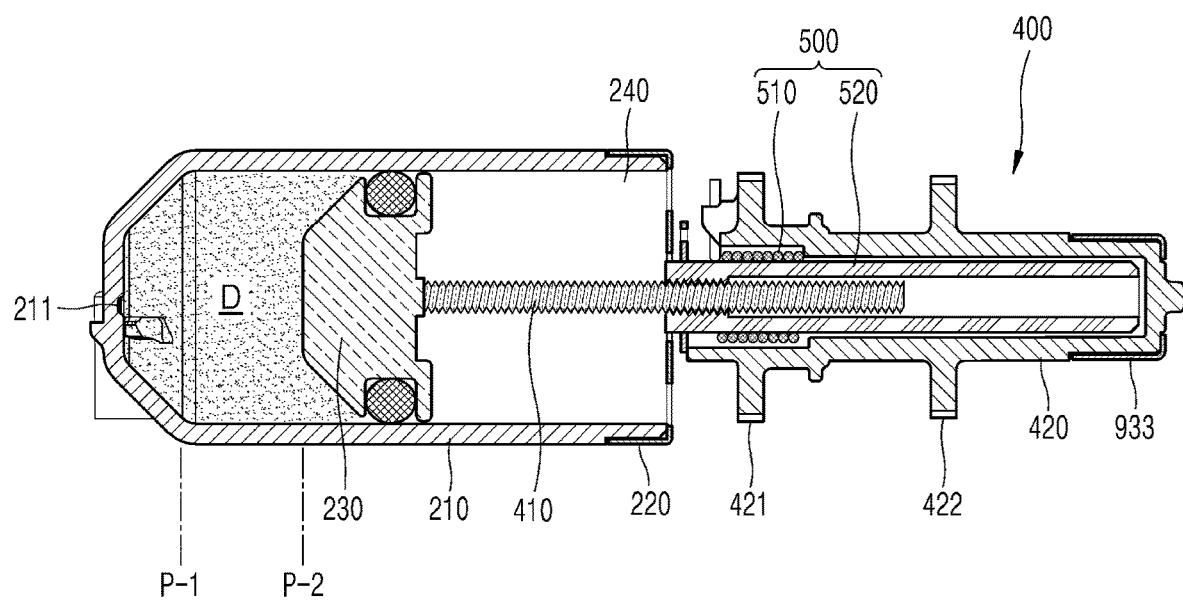

The coupler 510 is disposed outside the connecting member 520, and is spaced apart from the connecting member 520 at a predetermined interval when inactive (see FIGS. 10 and 11), and may connect the rod 410 and the driving wheel 420 when activated (see FIGS. 12 and 13). The coupler 510 is a part capable of applying an elastic force to the outside of the connecting member 520, and is not limited to a specific shape. However, in the following, for convenience of description, a case of a spring type will be mainly described.

The connecting member 520 may be arranged such that at least a part thereof is inserted into the rod 410. The connecting member 520 is disposed to cover the outside of the rod 410. The connecting member 520 may connect the driving module 300 and the rod 410 according to the operation of the coupler 510.

In one embodiment, the rod 410 and the connecting member 520 may each have a form of a screw and a screw thread. A screw thread is formed on an outer circumferential surface of the rod 410, and a screw thread is formed on an inner circumferential surface of the connecting member 520, so that the rod and the connecting member may be connected in a screw-coupling manner.

In one embodiment, the screw thread is formed on one end of the inner circumferential surface of the connecting member 520, but the screw thread may not be disposed on the other end.

Referring to FIG. 10, a screw thread is formed on an inner circumferential surface of a first section L1 of the connecting member 520, and the connecting member is screw-coupled with the rod 410 only in the first section L1. In addition, a diameter of the first section L1 corresponds to the rod 410 and may have a size of D1.

A screw thread is not formed on an inner circumferential surface of a second section L2 of the connecting member 520. In addition, a diameter D2 of the second section L2 may be set larger than the diameter D1 of the first section L1. In the second section L2, the connecting member 520 does not contact the rod 410.

A length of the first section L1 may be set so that the connecting member 520 overlaps with the coupler 510 when it moves backward. Referring to FIGS. 11 and 12, when the plunger 230 extends most rearward, at least a portion of the first section L1 is disposed to overlaps the coupler 510, that is, at least a portion is disposed to face the coupler 510. The length of the first section L1 may be set in the connecting member 520 so that the coupler 510 grips at least a portion of the first section L1 when the coupler 510 is activated.

Since the rod 410 is screwed only in the first section L1 of the connecting member 520, when the connecting member 520 rotates to move the rod 410 to the front, a load due to the screw-coupling between the connecting member 520 and the rod 410 may be reduced.

As illustrated in FIGS. 12 and 13, when the coupler 510 is activated, the coupler 510 grips the connecting member 520 and the connecting member 520 rotates as the driving wheel 420 rotates. Since the connecting member 520 and the rod 410 are screwed only in the first section L1, the connecting member 520 may move the rod 410 to the front even when the driving wheel 420 rotates with a small torque. That is, since the rod 410 and the connecting member 520 are screwed together only in the first section L1, the plunger 230 may move to the front even with a rather weak force by driving the driving unit 400.

The trigger member 600 may generate a mechanical signal through which the medical liquid of the medical liquid injection device 10 is injected. The trigger member 600 is rotatably disposed on one side of the third body 15, the trigger member 600 rotates to start driving the driving module 300, and at the same time, the clutch unit 500 may drive and connect the driving unit 400.

The trigger member 600 may rotate in one direction around a rotational axis. At this time, the trigger member 600 may apply force to the clutch unit 500 to couple the rod and the driving wheel 420.

In detail, when the user rotates the needle assembly 100, a knob of the needle assembly 100 presses an end of the trigger member 600, so that rotation of the trigger member 600 may be initiated. When the trigger member 600 rotates, the trigger member 600 presses the end of the coupler 510, the coupler 510 is combined with the connecting member 520, and the clutch unit 500 is activated.

The needle cover assembly 700 may be mounted under the needle assembly 100. The needle cover assembly 700 may prime air stored in the reservoir unit 200 before injecting the medical liquid. When the medical liquid is injected into the reservoir 210 through the medical liquid injector NI, the gas (air) remaining in the reservoir 210 may be discharged to the outside.

The needle cover assembly 700 may have a first cover 710, a second cover 720, a filter member 730 and an adhesive layer 740.

The first cover 710 may be disposed on a lower portion of the medical liquid injection device 10. The second cover 720 may be inserted into an opening of the first cover 710 and assembled. An insertion protrusion 711 inserted into the second body 14 and fixing the needle cover assembly 700 may be disposed on one side of the first cover 710.

The second cover 720 is assembled to the first cover 710, and the needle N and/or the cannula may be aligned at an center thereof. The second cover 720 may have a storage space penetrating in the center in a height direction and storing the medical liquid D.

The first cover 710 is stronger than the second cover 720. The first cover 710 is a part that is exposed to the outside and is made of a material with rather high rigidity. The second cover 720 is assembled to the first cover 710 and is formed of a material with less rigidity than the first cover 710 in order to be inserted into an opening of the third body 15.

A protrusion 721 inserted into the third body 15 may be provided at the center of the second cover 720. In addition, the second cover 720 includes the fixing protrusion 722, and the fixing protrusion 722 is inserted into the first cover 710, so that the first cover 710 and the second cover 720 may be assembled.

The filter member 730 is mounted on the second cover 720. The filter member 730 is disposed below the storage space of the second cover 720, and the gas such as the air passes through the filter member 730, but liquid such as the medical liquid does not pass through the filter member 730. Thus, the air discharged from the needle N passes through the filter member 730 and is discharged to the outside, but the medical liquid discharged from the needle may be stored in a storage space defined by the second cover 720 and the filter member 730.

The shape of the filter member 730 may change according to the amount of the medical liquid stored in the storage space. For example, when the medical liquid is filled in the storage space, the filter member 730 expands downward, so that the user may recognize that the medical liquid has flowed into the needle cover assembly 700.

The adhesive layer 740 is disposed on one side of the needle cover assembly 700, and may attach the needle cover assembly 700 to the attachment part 12.

The alarm unit 800 is disposed inside or outside the medical liquid injection device 10, and may notify the user of normal operation or malfunction of the medical liquid injection device 10.

For example, the alarm unit 800 is disposed below the housing 11 and is connected to the circuit board. The alarm unit 800 may deliver an alarm to an external user by generating a warning sound or generating a light.

Figure 6:
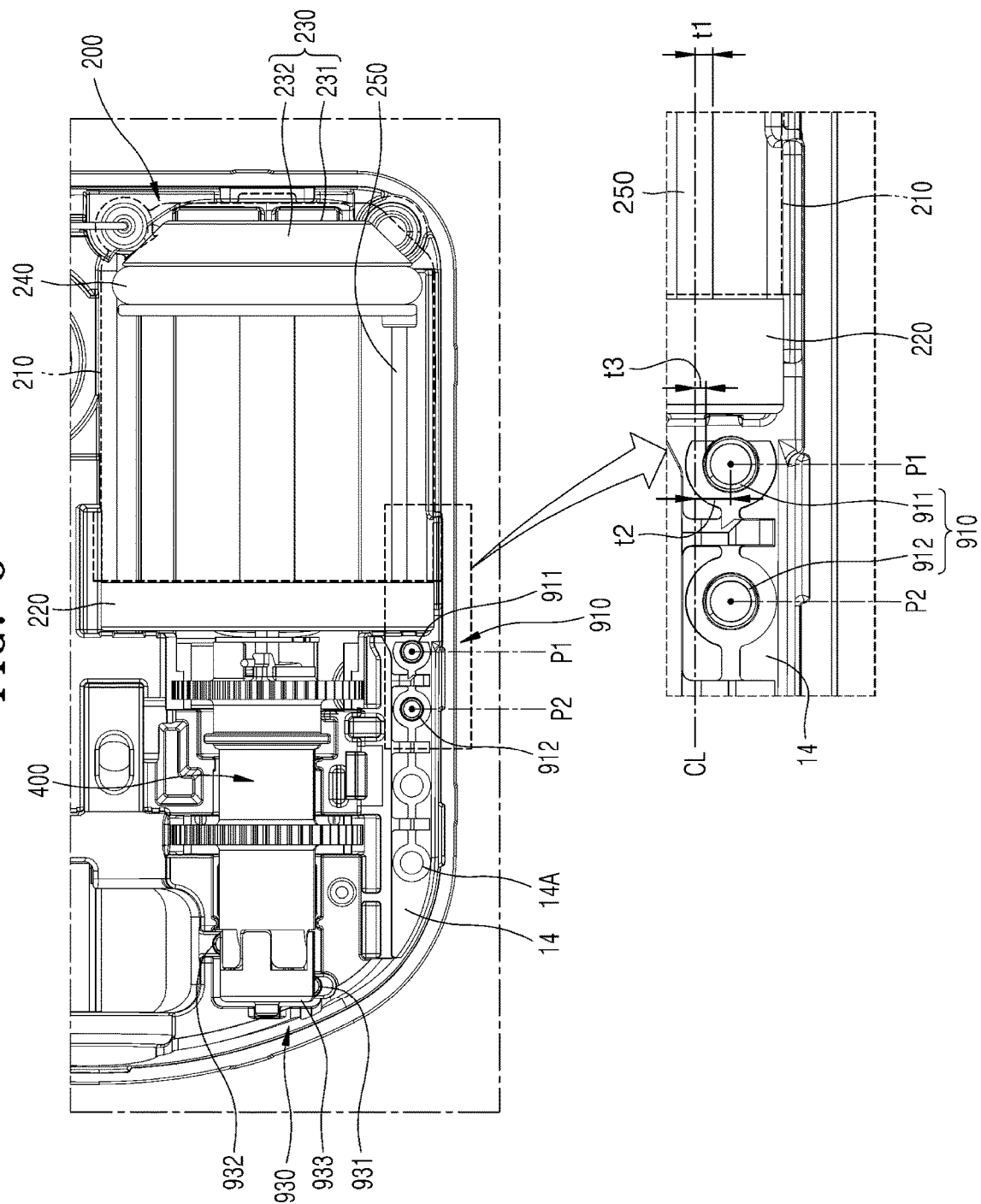
FIGS. 6 and 7 are plan views illustrating an operation of sensing a flow rate of a reservoir.
Figure 7:
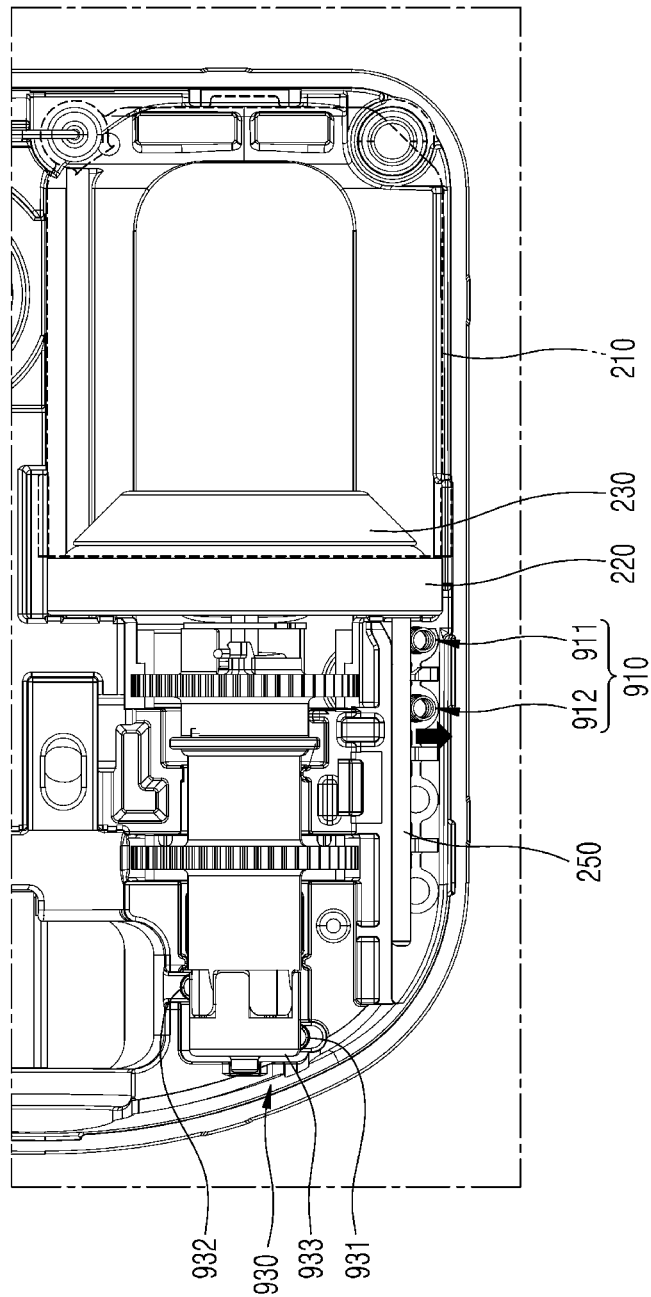
Figure 8:
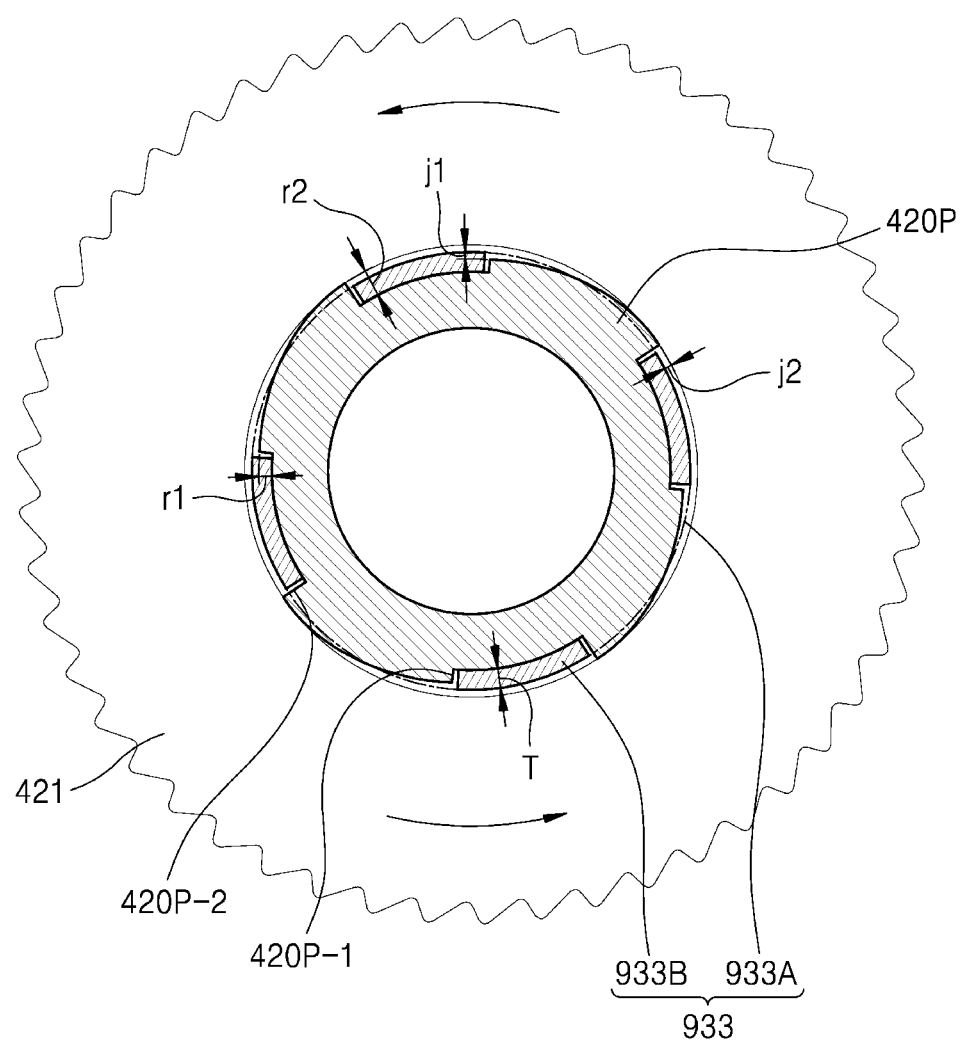
FIG. 8 is a cross-sectional view illustrating a cross section of an end of a driving unit of FIG. 5.
Figure 9:
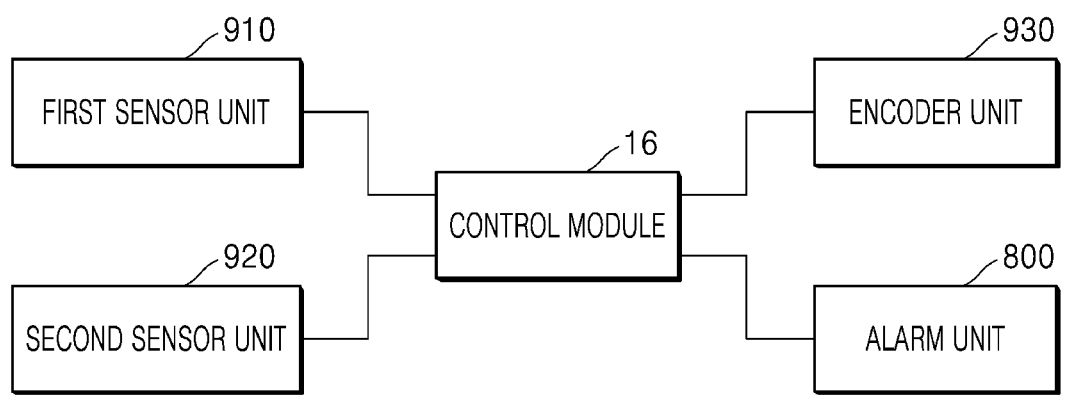
FIG. 9 is a block diagram illustrating some configurations of the medical liquid injection device of FIG. 2.

FIGS. 6 and 7 are plan views illustrating an operation of sensing a flow rate of a reservoir 210, FIG. 8 is a block diagram illustrating some configurations of the medical liquid injection device 10 of FIG. 2, and FIG. 9 is a block diagram illustrating some configurations of the medical liquid injection device 10 of FIG. 2.

Referring to FIGS. 4 to 9, a plurality of sensor units may measure driving of the medical liquid injection device 10. The plurality of sensor units may measure the amount of medical liquid stored in the reservoir 210, whether the driving module 300 is driven, whether the driving unit 400 is driven, a rotation angle of the driving wheel 420, a moving distance of the plunger 230, and the like.

Each sensor units may have a plurality of contact ends. The contact end may measure each event or data by measuring electrical contact.

A position of any one end of the contact end may be changed by contact with another part, and may be returned to its original position by restoring force when contact with the other part is released.

In one embodiment, the contact end may have an elastic spring shape. In the contact end, a first end portion 900A is connected to the control module 16, which is the circuit board, and a second end portion 900B extends from the first end portion 900A but may come into contact with the connector member 250.

A diameter of the first end portion 900A may be set larger than a diameter of the second end portion 900B. Since the diameter of the first end portion 900A is larger than the diameter of the second end portion 900B, the first end portion 900A may be firmly supported on the circuit board. The first end portion 900A is stably supported by a control module 160, and a position or shape of the second end portion 900B is easily deformed to stably maintain contact with other parts.

A length of the first end portion 900A may be set smaller than a length of the second end portion 900B. Since the length of the first end portion 900A is shorter than the length of the second end portion 900B, the first end portion 900A may be firmly supported on the circuit board. The first end portion 900A is stably supported by a control module 160, and a position or shape of the second end portion 900B is easily deformed to stably maintain contact with other parts.

In particular, since the diameter of the second end portion 900B is smaller than the diameter of the first end portion 900A, or the length of the second end portion 900B is set to be longer than the length of the first end portion 900A, the second end portion 900B is easily deformed in position or shape, and may stably maintain contact with other parts even if the second end portion 900B contacts other parts such as the connector member 250, a base cover 933, and the like.

The first sensor unit 910 is disposed adjacent to the reservoir unit 200. The first sensor unit 910 may be disposed on a moving path of the connector member 250. The first sensor unit 910 may include the plurality of contact ends, and the plurality of contact ends may be mounted in a fixing groove 14A of the second body 14. While moving, the connector member 250 may contact at least one of the plurality of contact ends.

As an embodiment, the first sensor unit 910 may include a first contact end 911 and a second contact end 912. The first contact end 911 and the second contact end 912 are spaced apart from each other, and the connector member 250 may linearly move to make contact with the first contact end 911 and/or the second contact end 912.

The connector member 250 may contact the first contact end 911 at a first position P1 and contact the second contact end 912 at a second position P2.

Referring to FIGS. 6, 10 and 11, in a process of injecting the medical liquid D into the reservoir 210, the connector member 250 first contacts the first contact end 911 at the first position P1 (the plunger 230 is at a P-1 position), and then the connector member 250 contacts the second contact end 912 at the second position P2 (the plunger 230 is at a P-2 position).

As an example, the connector member 250 may electrically connect the first contact end 911 and the second contact end 912. When the first contact end 911 and the second contact end 912 are electrically connected through the connector member 250, the control module 16 may recognize a specific event of the reservoir unit 200.

For example, when the connector member 250 contacts the first contact end 911 and the second contact end 912, the first sensor unit 910 may sense that the medical liquid stored in the reservoir 210 is stored in a first reference amount (e.g., 10%, 20%, 30%, etc.).

When recognizing that the medical liquid D is stored in the reservoir 210 as the set first reference amount, the control module 16 may awake the medical liquid injection device 10. That is, the control module 16 may confirm that a certain amount of medical liquid is stored in the reservoir 210, and start partially driving to preheat the medical liquid injection device 10 (first mode).

In another embodiment, the connector member 250 may contact at least one of the contact ends of the first sensor unit 910 to generate an electrical signal. The control module 16 recognizes a first event when the connector member 250 contacts the first contact end 911, and the control module 16 recognizes a second event when the connector member 250 contacts the second contact end 912.

For example, the connector member 250 may awake the medical liquid injection device 10 by contacting the first contact end 911, and may sense the amount of medical liquid stored in the medical liquid injection device 10 by contacting the second contact end 912.

For example, the connector member 250 may primarily sense the amount of medical liquid stored in the reservoir 210 while awaking the medical liquid injection device 10 by contacting the first contact end 911, and may secondarily sense the amount of medical liquid stored in the medical liquid injection device 10 by contacting the second contact end 912.

As illustrated in FIGS. 6, 12, and 13, in the process of discharging the medical liquid D through the needle N, the connector member 250 first releases contact with the second contact end 912 at the second position P2 (the plunger 230 is at the P-2 position), and then the connector member 250 is out of contact with the first contact end 911 at the first position P1 (the plunger 230 is at the P-1 position).

In one embodiment, when the connector member 250 maintains contact with the first contact end 911 and the second contact end 912 and the contact with the second contact end 912 is disconnected, the electrical connection between the first contact end 911 and the second contact end 912 is disconnected. When the first contact end 911 and the second contact end 912 are electrically disconnected, the control module 16 may recognize a specific event of the reservoir unit 200.

In detail, when the second contact end 912 is disconnected, the control module 16 may generate a signal indicating that the medical liquid D stored in the reservoir 210 is insufficient. The control module 16 generates an alarm signal and transmits the alarm signal to the controller 30, the user terminal 20, and/or the alarm unit 800 so that the user may recognize the amount of the medical liquid.

In addition, when a third mode is set in the medical liquid injection device 10, a forward distance of the plunger 230 within the reservoir 210 is accurately measured, and the amount of the medical liquid stored in the reservoir 210 may be precisely measured and monitored, by using the second sensor unit 920 and/or an encoder unit 930.

In another embodiment, the connector member 250 may release contact with at least one of the contact ends of the first sensor unit 910 to recognize different events. The control module 16 recognizes a third event when the connector member 250 releases contact with the second contact end 912, and the control module 16 may recognize a fourth event when the connector member 250 releases contact with the second contact end 912.

For example, when the connector member 250 releases contact with the second contact end 912, the control module 16 may transmit an alarm signal to the user, and when the contact with the first contact end 911 is released, the control module 16 may forcibly terminate the medical liquid injection device 10, may continuously generated the alarm signal in the user terminal 20, may reduce the amount of the medical liquid injected to the user, or may increase an injection cycle.

Referring to FIG. 6, the first sensor unit 910 may be spaced apart from a center line CL of the longitudinal direction of the connector member 250, and a surface of the contact end may be in contact with a surface of the connector member 250.

The connector member 250 extends based on the center line CL and moves linearly along the center line CL. Also, an outer circumferential surface of the connector member 250 is spaced apart from the center line CL by a length of t1. A center of the plurality of contact ends is spaced apart from the center line CL by t2, and the surface of the plurality of contact ends is spaced apart from the center line CL by t3.

Since a size of t1 is set larger than a size of t3, when the connector member 250 moves backward along the center line CL, it may contact the first contact end 911 at the point of P1 and contact the second contact end 912 at the point of P2. Also, when the connector member 250 moves to the front along the center line CL, the contact with the second contact end 912 may be released at the point of P2 and the contact with the first contact end 911 may be released at the point of P1.

The second sensor unit 920 may sense whether the driving module 300 and/or the driving unit 400 are driven. The driving module 300 and the driving wheel 420 are operatively connected by the connector CN. When the driving module 300 moves linearly, the connector rotates repeatedly around the rotational axis, and both ends of the connector CN alternately apply pressure to the first connection end 421 and the second connection end 422 of the driving wheel 420, so that the driving wheel 420 rotates. The second sensor unit 920 may measure whether the connector CN rotates around the rotational axis and the number of rotations.

The second sensor unit 920 may have a 1A-contact end 921 and a 2A-contact end 922. When the connector CN contacts the 1A-contact end 921, the second sensor unit 920 measures that the connector CN applied any one of the first connection end 421 and the second connection end 422. When the connector CN contacts the 2A-contact end 922, the second sensor unit 920 measures that the connector CN applied the other one of the first connection end 421 and the second connection end 422.

The encoder unit 930 is disposed at one end of the driving unit 400 to measure rotation of the driving unit 400. The encoder unit 930 may measure rotation of the driving wheel 420.

The encoder unit 930 may have the base cover 933 having a 1B-contact end 931, a 2B-contact end 932, and a cover end 933A and a tooth end 933B.

The 1B-contact end 931 is disposed at an end of the base cover 933 and may always maintain contact with the base cover 933. The 1B-contact end 931 may maintain contact with the cover end 933A.

In the drawing, it is illustrated that the 1B-contact end 931 is disposed on the opposite side of the 2B-contact end 932, but is not limited thereto. For example, the 1B-contact end 931 and the 2B-contact end 932 may be disposed on the same side of the driving wheel 420. Also, the 1B-contact end 931 may be disposed behind the rear of the driving wheel 420.

The 2B-contact end 932 is disposed at the end of the base cover 933 and spaced apart from the 1B-contact end 931. The 2B-contact end 932 is disposed to come into contact with the tooth end 933B, and may be contacted or released according to the rotation of the driving wheel 420.

The base cover 933 is inserted into one end of the driving wheel 420. The cover end 933A extends to circumnavigate the outer circumferential surface of the driving wheel 420, but the plurality of tooth ends 933B extend from the cover end 933A and may be spaced apart from each other along the outer circumferential surface of the driving wheel 420. The tooth end 933B may extend along the longitudinal direction of the driving wheel 420 from the cover end 933A.

In one embodiment, a width W1 of the tooth end 933B may be set smaller than a distance W2 between neighboring tooth ends. Since the width W1 is set shorter than the distance W2, the 2B-contact end 932 may reduce an error generated when contacting the tooth end 933B.

Referring to FIG. 8, the tooth end 933B may be inserted into a space between protruding ends 420P of the driving wheel 420. Since the protruding end 420P are made of non-conductive material and the tooth end 933B is made of conductive material, the 1B-contact end 931 and the 2B-contact end 932 are not electrically connected when the 2B-contact end 932 contacts the protruding end 420P, but the 1B-contact end 931 and the 2B-contact end 932 may be electrically connected when the 2B-contact end 932 contacts the tooth end 933B.

The protruding end 420P have a first wall 420P-1 and a second wall 420P-2, and the first wall 420P-1 and the second wall 420P-2 form a boundary with the tooth end 933B. As the connector CN rotates, the driving wheel 420 moves counterclockwise as illustrated in FIG. 8.

A height of the protruding end 420P in a radial direction may vary along the circumferential direction of the driving wheel 420. The height of the protruding end 420P may be defined as a distance from a bottom surface of the tooth end 933B to an outer circumferential surface in the radial direction. Since the height of the protruding end 420P changes in the circumferential direction of the driving wheel 420, a step may be formed between the tooth end 933B and the protruding end 420P.

For example, a height of the first wall 420P-1 may be defined as r1, and a height of the second wall 420P-2 may be defined as r2. The r1 may be set smaller than the r2.

For example, the height r1 of the first wall 420P-1 may be set smaller than a height T of the tooth end 933B, and the height r2 of the second wall 420P-2 may be set larger than the height T of the tooth end 933B.

For example, the height of the protruding end 420P may gradually increase from the first wall 420P-1 to the second wall 420P-2.

For example, the first wall 420P-1 is disposed under a radial direction of an outermost line of the cover end 933A, and the second wall 420P-2 is disposed above the radial direction of the outermost line of the cover end 933A. Accordingly, a portion of the protruding end 420P is disposed below the outermost line of the cover end 933A, and another portion is disposed above the outermost line of the cover end 933A.

When the driving wheel 420 rotates, when the 2B-contact end 932 contacts the tooth end 933B, the 2B-contact end 932 contacts the tooth end 933B at a certain position. However, when the 2B-contact end 932 contacts the protruding end 420P, the 2B-contact end 932 contacts the protruding end 420P while changing a contact position.

When the driving wheel 420 rotates, when the 2B-contact end 932 passes the boundary between the tooth end 933B and the protruding end 420P, the position of the 2B-contact end 932 changes according to the step between the tooth end 933B and the protruding end 420P.

In detail, when the 2B-contact end 932 passes through the first wall 420P-1 at the tooth end 933B, a positional change and an impact according to the step of the 2B-contact end 932 occur by a step of j1. When the 2B-contact end 932 passes through the tooth end 933B at the second wall 420P-2, a positional change and an impact according to the step of the 2B-contact end 932 occur by a step of j2.

When the 2B-contact end 932 contacts the tooth end 933B, the 1B-contact end 931 and the 2B-contact end 932 are electrically connected, and the encoder unit 930 senses an electrical connection signal. When the driving wheel 420 further rotates and the 2B-contact end 932 contacts the protruding end 420P, the 2B-contact end 932 is electrically disconnected. The encoder unit 930 may measure the rotation angle and rotation speed of the driving wheel 420 by measuring whether the 1B-contact end 931 and the 2B-contact end 932 are electrically connected or disconnected, and a number of electrical connections.

To increase a sensing accuracy of the encoder unit 930, the 2B-contact end 932 is electrically shorted exactly when moving from the tooth end 933B to the first wall 420P-1, and the 2B-contact end 932 must be electrically connected exactly when moving from the second wall 420P-2 to the tooth end 933B.

Since the position of the 2B-contact end 932 rapidly changes when the 2B-contact end 932 passes through the step j1 and/or j2 between the protruding end 420P and the tooth end 933B, the 2B-contact end 932 is exactly electrically shorting or connecting, thereby increasing the accuracy of the encoder unit 930.

Figure 14:
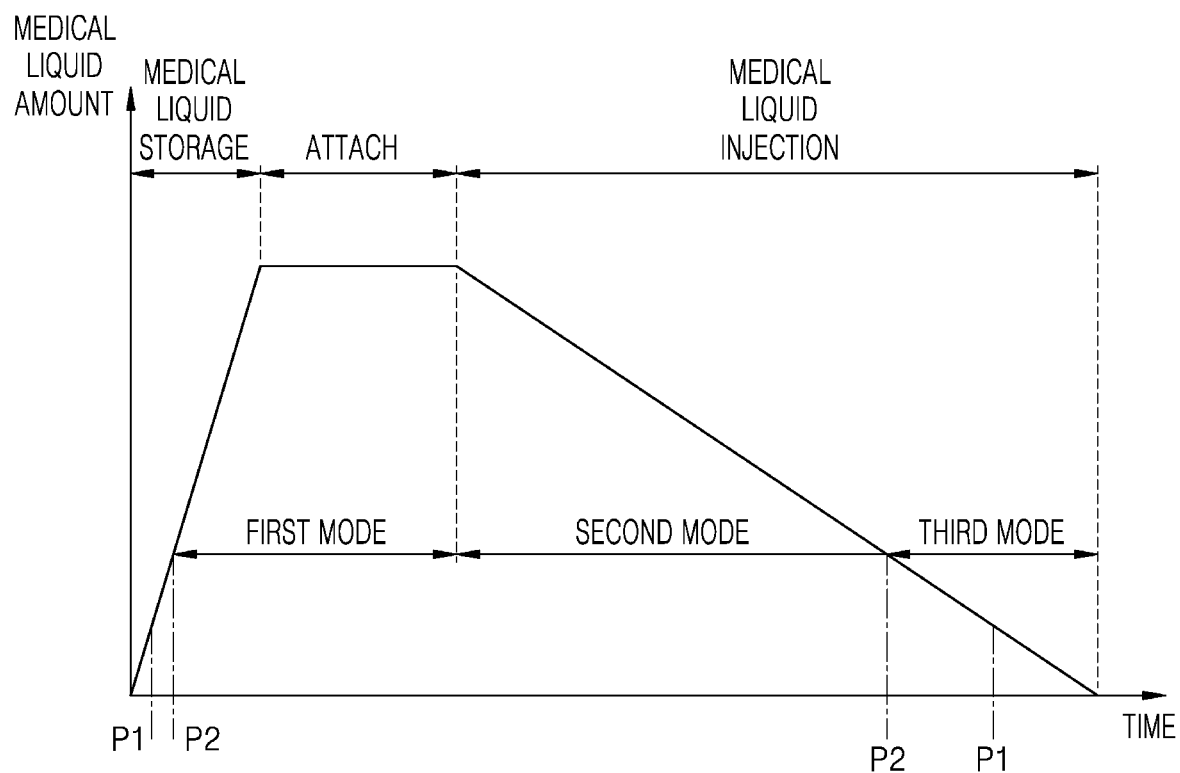
FIG. 14 is a graph illustrating a change in medical liquid amount and a change in driving mode according to driving of the medical liquid injection device.

FIGS. 10 to 13 are cross-sectional views illustrating an operation of injecting a medical liquid into the reservoir 210, storing the medical liquid, and discharging the medical liquid through a needle N, and FIG. 14 is a graph illustrating a change in medical liquid amount and a change in driving mode according to driving of the medical liquid injection device 10.

Referring to FIGS. 10 to 14, the process of storing the medical liquid D in the reservoir 210 before attaching the medical liquid injection device 10 to the user, then discharging the medical liquid D from the reservoir 210 with the needle N to inject the medical liquid D into the user is explained as follows.

<Medical Liquid Storage Stage>

The user injects the medical liquid into the reservoir unit 200 of the medical liquid injection device 10 by using the external medical liquid injector (not illustrated). Referring to FIG. 10, before the medical liquid injection, the plunger 230 is disposed at the front end of the reservoir 210, and the rod 410 is assembled to the connecting member 520 at the rear end of the plunger 230. At this time, since the coupler 510 does not grip the connecting member 520, the driving wheel 420 is not connected to the rod 410.

The user puts the medical liquid D to be injected into the medical liquid injector (not illustrated) and inserts the medical liquid injector into the inlet end of the reservoir unit 200. At this time, the air remaining inside the reservoir 210 may be primed.

In detail, during the assembly process of the reservoir unit 200, air remains between the reservoir 210 and the plunger 230. If the medical liquid is injected while air remains in the reservoir 210, there is a risk that the air will also be injected into the user, so an action to remove the air (priming action) is required.

When the medical liquid starts to flow into the reservoir 210 from the medical liquid injector, it flows between the inner surface of the reservoir 210 and the plunger 230, and pushes the remaining gas to the needle N. At this time, the gas may move along a guide groove 211. That is, the gas remaining inside the reservoir 210 may be discharged to the needle N along the guide of the guide groove 211 by the introduced medical liquid D. The gas passing through the needle N moves to the needle cover assembly 700, passes through the filter member 730 of the needle cover assembly 700, and is discharged to the outside. The gas remaining inside the reservoir 210 is quickly discharged to the outside by the guide of the guide groove 211, and the gas in the reservoir 210 may be removed.

According to the amount of the medical liquid D injected into the reservoir 210, the first sensor unit 910 may be driven.

When the plunger 230 passes the point P-1 according to the injection of the medical liquid D, the connector member 250 contacts the first contact end 911 at the first position P1. Then, when the plunger 230 passes the point P-2, the connector member 250 contacts the second contact end 912 at the second position P2.

In one embodiment, when the connector member 250 electrically connects the first contact end 911 and the second contact end 912, the first mode is driven. The first mode is a mode to awake the medical liquid injection device 10, and the medical liquid injection device 10 may be preheated in advance so that the medical liquid injection device 10 is immediately driven when it is attached to the user. In addition, the user may be informed through the user terminal 20 that the set first reference amount of the medical liquid D is stored in the reservoir 210 in advance, thereby informing the user to use the medical liquid injection device 10 in advance.

In another embodiment, if the connector member 250 is connected to the first contact end 911, the control module 16 may recognize it as the first event, and if it is connected to the second contact end 912, the control module 16 may recognize it as the second event. That is, when the connector member 250 contacts different contact ends, different events may be recognized and the events may be delivered to the user.

<Attach Stage>

As illustrated in FIG. 11, after the medical liquid D is stored in the reservoir 210, the medical liquid injection device 10 is attached to the user. Since gas in the reservoir 210 is removed (priming operation is completed) through the needle cover assembly 700 in the medical liquid storage stage described above, the needle cover assembly 700 is removed from the medical liquid injection device 10.

The user attaches the medical liquid injection device 10 to the user, rotates the needle assembly 100, and inserts the needle N and the cannula into the skin. The needle N is inserted into the skin together with the cannula, and may guide the cannula to be inserted into the skin.

Afterwards, the needle N is withdrawn from the skin, but remains connected to the cannula. If the user further rotates the needle assembly 100, the needle N moves upward while the cannula is inserted into the skin. At least a part of the cannula and the needle N are connected, forming and maintaining the path through which the medical liquid moves.

<Medical Liquid Injection Stage—Second Mode>

The driving module 300 and the driving unit 400 are driven at substantially the same time as the cannula and the needle N are inserted into the user. The medical liquid injection device 10 may inject the medical liquid D into the user according to the set cycle and injection amount in the second mode.

When the user rotates the needle assembly 100 to insert the needle N and the cannula into the skin, the trigger member 600 drives the driving module 300. When the driving module 300 is driven, the connector CN rotates the driving wheel 420 while rotating around the rotational axis. The connector CN may rotate the driving wheel 420 in units of 1 tooth while alternately applying pressure to the first connection end 421 and the second connection end 422.

When the user rotates the needle assembly 100, the trigger member 600 may activate the coupler 510 as illustrated in FIG. 12. When the coupler 510 grips the outside of the connecting member 520, the driving wheel 420, the coupler 510 and the connecting member 520 are integrated into one body. Therefore, when the driving wheel 420 rotates, the connecting member 520 also rotates, and the rod 410 moves to the front.

When the rod 410 moves to the front, the plunger 230 also moves to the front, and the medical liquid may be discharged to the needle N. Accordingly, the medical liquid may be injected into the user according to the set driving cycle and driving speed of the driving module 300.

At this time, the second sensor unit 920 may measure rotation of the connector CN. The 1A-contact end 921 and the 2A-contact end 922 of the second sensor unit 920 alternately contact the end of the corresponding connector CN. The second sensor unit 920 senses the contact between the 1A-contact end 921 and one end of the connector CN, and the contact between the 2A-contact end 922 and the other end of the connector CN.

In one embodiment, when the contact end of the second sensor unit 920 and the connector CN come into contact, the second sensor unit 920 may sense the electrical signal. In another embodiment, when the contact end of the second sensor unit 920 and the connector CN come into contact, the second sensor unit 920 may sense an impact signal according to an impact.

The second sensor unit 920 may measure whether the driving module 300 and the connector CN are driven based on the rotation measurement data of the connector, may measure whether the driving wheel 420 is driven by the connector CN, may measure the rotation angle and/or the rotation speed of the driving wheel 420, or may measure the moving distance of the plunger 230 and the injection amount of the medical liquid by the rotation of the driving wheel 420.

When the driving wheel 420 rotates, the encoder unit 930 may measure the rotation angle, the rotation speed, etc. of the driving wheel 420. The 1B-contact end 931 maintains electrical contact with the cover end 933A, but the 2B-contact end 932 maintains electrical contact with the tooth end 933B, but the electrical contact may be released when the 2B-contact end leaves the tooth end 933B.

The encoder unit 930 may measure data related to the rotation of the driving wheel 420 by measuring the electrical connection signal and/or an electrical release signal. The control module 16 may calculate the rotation angle and rotation speed of the driving wheel 420 based on the data measured by the encoder unit 930, and calculate the moving distance of the plunger 230 and the discharge amount of the medical liquid based on these.

<Medical Liquid Injection Stage—Third Mode>

When the plunger 230 is positioned at the P-2 position and the connector member 250 is positioned at the second position P2, the first contact end 911 and the second contact end 912 are electrically separated from the first sensor unit 910. The control module 16 may activate the third mode when the first sensor unit 910 is electrically released.

In the third mode, the control module 16 may deliver an alarm signal indicating that the amount of stored medical liquid corresponds to a second reference amount to the user through the user terminal 20, the controller 30, and/or the alarm unit 800. The second reference amount may be defined as the amount of medical liquid recognized by the driving module 300 at the time of driving the third mode. The control module 16 informs the user that the amount of medical liquid remaining in the reservoir 210 is the preset second reference amount, so that the user may prepare to replace the medical liquid injection device 10.

In one embodiment, the first reference amount may be set to the same medical liquid storage amount as the second reference amount. When the connector member 250 contacts or releases contact with the second contact end 912 as the plunger 230 advances or retreats, since the position of the plunger 230 in the reservoir 210 is the same, the first reference amount and the second reference amount may be set to be the same.

In another embodiment, the first reference amount may be set to a larger medical liquid storage amount than the second reference amount. The first reference amount is a reference value set for operation of the first mode, and may be set to be substantially equal to the amount of medical liquid stored in the reservoir 210. The second reference amount is the amount of medical liquid recognized by the driving module 300 at a start of the third mode, and may be set to be smaller than the amount of medical liquid actually remaining in the reservoir 210 to have a margin.

Since the second reference amount is set to be smaller than the actual amount of medical liquid stored in the reservoir 210, the reservoir 210 has a margin corresponding to the difference between the actual residual amount of the medical liquid and the second reference amount. Even if the medical liquid injection device 10 informs that there is no medical liquid, the medical liquid left in the reservoir 210 may be used more, thereby eliminating sudden medical liquid disconnection or accidents, thereby increasing the safety of the medical liquid injection device 10.

Since the residual amount of medical liquid is important in the third mode, the control module 16 may calculate the injection amount of the medical liquid and the residual amount of the medical liquid in the reservoir 210 very precisely in the third mode. In the third mode, based on the data obtained from the second sensor unit 920 and the encoder unit 930, the control module 16 may accurately measure the rotation angle of the driving wheel 420 and the moving distance of the plunger 230 to strictly calculate the amount of medical liquid discharged and the residual amount of the medical liquid in the reservoir 210. The residual amount of the medical liquid accurately calculated in the third mode is delivered to the user in real time, so the user may recognize a risk.

In one embodiment, the medical liquid injection device 10 may accurately count the amount of medical liquid remaining in the reservoir 210 only in the third mode. In the second mode, the amount of medical liquid stored in the reservoir 210 exceeds the preset range (i.e., the second reference amount), so the amount of medical liquid in the reservoir 210 is not accurately counted, but in the third mode, the amount of medical liquid stored in the reservoir 210 is measured may be quantitatively counted. Since the storage amount of medical liquid is accurately counted only at a level where the alarm for the amount of medical liquid stored in the medical liquid injection device 10 is required, a control load of the medical liquid injection device 10 may be reduced.

Figure 15:
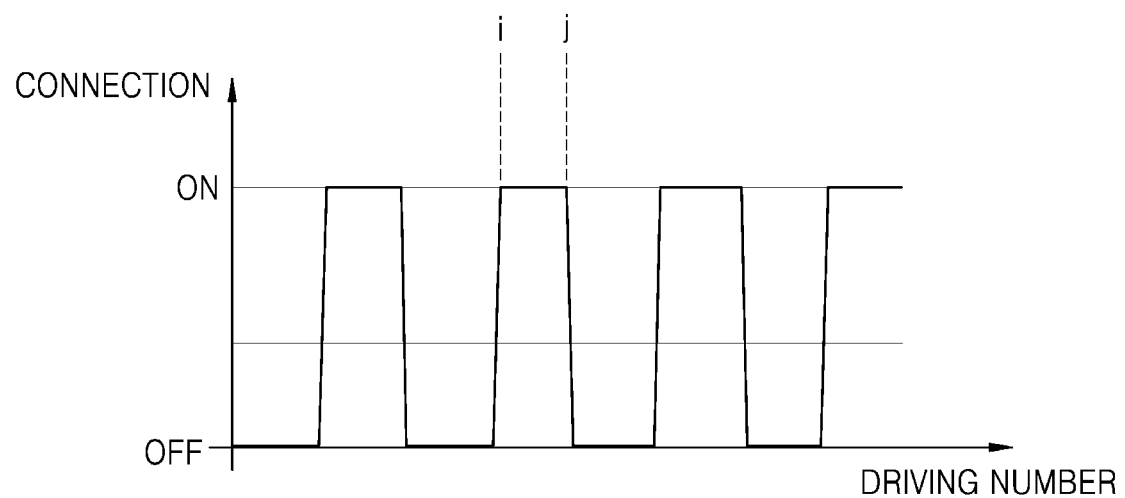
FIG. 15 is a graph illustrating signal sensing of an encoder unit.

FIG. 15 is a graph illustrating signal sensing of an encoder unit 930.

Referring to FIGS. 8 and 15, the encoder unit 930 may measure data such as the rotation angle, the rotation speed, etc. of the driving wheel 420 by measuring the electrical connection signal.

The control module 16 may accurately calculate the amount of medical liquid stored in the reservoir 210 and the amount of medical liquid injected to the user based on the data measured by the encoder unit 930.

Since the electrical connection is ON/OFF, the encoder unit 930 may measure the rotation angle of the driving wheel 420 based on an ON time point i and/or an OFF time point j, so that the load of the control module 16 may be reduced.

Specifically, the control module 16 may determine a contact pattern for the encoder unit 930. Referring to FIG. 5, the encoder unit 930 may have the 1B-contact end 931, the 2B-contact end 932, a base cover 933 having the cover end 933A and the tooth end 933B. The 1B-contact end 931 is disposed at an end of the base cover 933 and may always maintain contact with the base cover 933. The 1B-contact end 931 may maintain contact with the cover end 933A.

The 2B-contact end 932 is disposed at the end of the base cover 933 and spaced apart from the 1B-contact end 931. The 2B-contact end 932 is disposed to come into contact with the tooth end 933B, and may be contacted or released according to the rotation of the driving wheel 420.

In one embodiment, when the 2B-contact end 932 contacts the tooth end 933B of the base cover 933 while the 1B-contact end 931 maintains contact with the cover end 933A of the base cover 933, the control module 16 may determine the current contact pattern as a first contact pattern. The first contact pattern is a state in which the 1B-contact end 931 and the 2B-contact end 932 are electrically connected, and at this time, the control module 16 may receive a high signal.

In addition, when the 2B-contact end 932 is released from contact with the tooth end 933B of the base cover 933 while the 1B-contact end 931 maintains contact with the cover end 933A of the base cover 933, the control module 16 may determine the current contact pattern as a second contact pattern. The second contact pattern is a state in which the 1B-contact end 931 and the 2B-contact end 932 are not electrically connected, and at this time, the control module 16 may receive a low signal.

Referring to FIG. 8, the tooth end 933B may be inserted into the space between the protruding ends 420P of the driving wheel 420. Since the protruding end 420P are made of non-conductive material and the tooth end 933B is made of conductive material, the 1B-contact end 931 and the 2B-contact end 932 are not electrically connected when the 2B-contact end 932 contacts the protruding end 420P, but the 1B-contact end 931 and the 2B-contact end 932 may be electrically connected when the 2B-contact end 932 contacts the tooth end 933B.

Referring to FIG. 15, a time point when the contact pattern is changed from the second contact pattern to the first contact pattern may correspond to the ON time point i when the electrical connection is ON, a time when the first contact pattern is changed to the second contact pattern may correspond to the OFF time point j when the electrical connection is OFF.

The control module 16 may check whether the current contact pattern remains as the first contact pattern or the second contact pattern and calculate a number of confirmations. Specifically, the control module 16 may receive the high signal or the low signal by applying a current to the encoder unit 930 whenever the teeth of the driving wheel 420 move once.

When the 1B-contact end 931 and the 2B-contact end 932 are electrically connected, the control module 16 may receive the high signal. Also, when the 1B-contact end 931 and the 2B-contact end 932 are not electrically connected, the control module 16 may receive the low signal. The control module 16 may determine that the current contact pattern is the first contact pattern when the high signal is received, and the control module 16 may determine that the current contact pattern is the second contact pattern when the low signal is received.

For example, in order for the driving wheel 420 to rotate once, the teeth of the driving wheel 420 may move 100 times, and the protruding end 420P and the tooth end 933B may be alternately located around the driving wheel 420 by four. In this case, when the driving wheel 420 rotates once, the contact pattern is changed eight times. That is, one contact pattern corresponds to 12.5 tooth movements. At this time, if the number of confirmations for one contact pattern exceeds 13 times, it indicates that the driving wheel 420 rotates less than intended, which corresponds to a situation in which the medical liquid is under-injected. As another example, if the number of confirmations for one contact pattern is less than 12, and another contact pattern is confirmed, it indicates that the driving wheel 420 has rotated more than intended, which corresponds to a situation in which the medical liquid is over-injected.

Hereinafter, a method for determining a situation in which the medical liquid is under-injected or over-injected will be described in detail.

Figure 16:
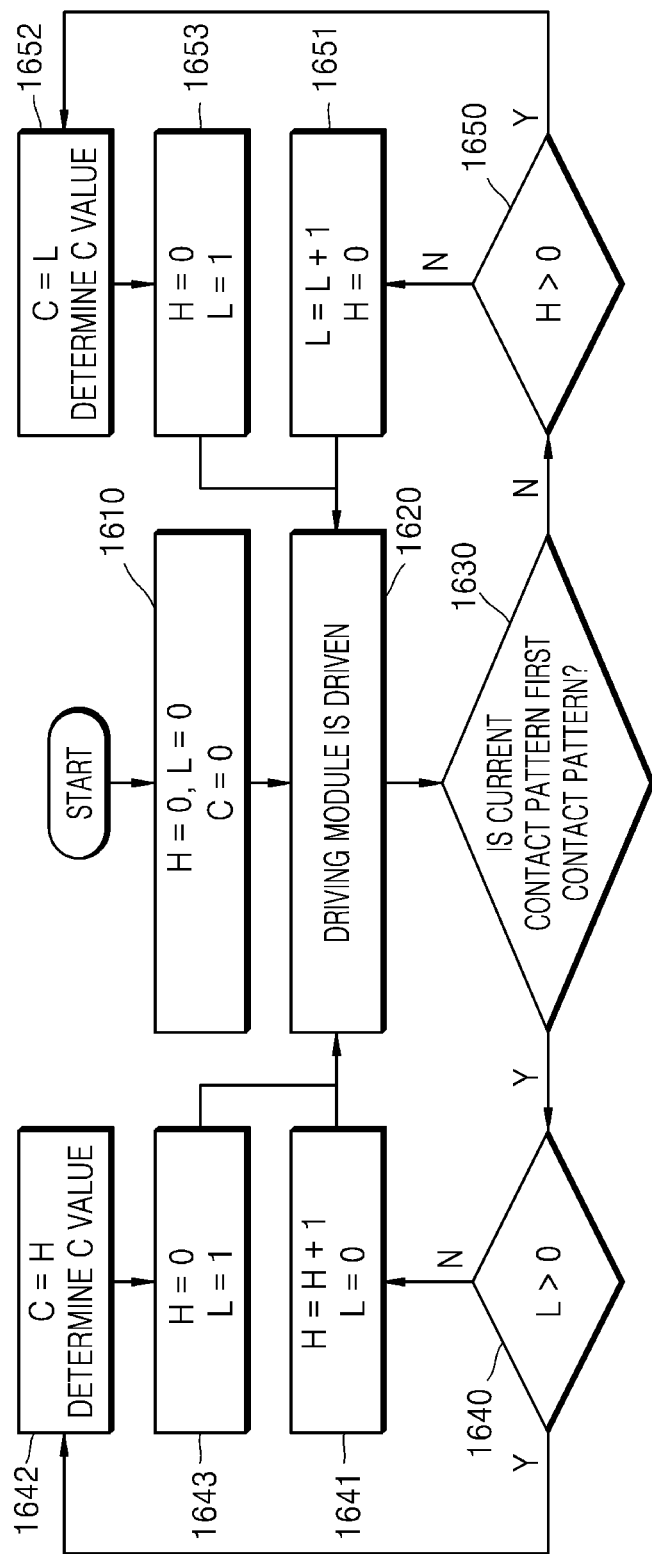
FIG. 16 is a flowchart illustrating a method of determining over-injection or under-injection of the medical liquid when a contact pattern is changed according to an embodiment.

FIG. 16 is a flowchart illustrating a method of determining over-injection or under-injection of the medical liquid when a contact pattern is changed according to an embodiment.

Referring to FIG. 16, in step 1610, H, L and C are all set to 0. H represents a number of confirmations of the first contact pattern, L represents a number of confirmations of the second contact pattern, and C represents an evaluation value used to determine the over-injection or the under-injection.

In step 1620, the driving module 300 may be driven.

As the driving module 300 is driven, the medical liquid stored in the reservoir 210 is discharged to the outside through the medical liquid injector NI. When the driving module 300 is driven once, the teeth of the driving wheel 420 of the driving unit 400 connected to the driving module 300 moves once.

In step 1630, the control module 16 may determine the current contact pattern.

The control module 16 may receive the high signal or the low signal by applying current to the encoder unit 930 whenever the teeth of the driving wheel 420 move once. The control module 16 may determine that the current contact pattern is the first contact pattern when the high signal is received, and the control module 16 may determine that the current contact pattern is the second contact pattern when the low signal is received.

When the 2B-contact end 932 contacts the tooth end 933B of the base cover 933 while the 1B-contact end 931 maintains contact with the cover end 933A of the base cover 933, the control module 16 may determine the current contact pattern as the first contact pattern. In addition, when the 2B-contact end 932 is released from contact with the tooth end 933B of the base cover 933 while the 1B-contact end 931 maintains contact with the cover end 933A of the base cover 933, the control module 16 may determine the current contact pattern as the second contact pattern.

When the current contact pattern is the first contact pattern, step 1640 is performed. On the other hand, when the current contact pattern is the second contact pattern, the process proceeds to step 1650.

In step 1640, the control module 16 may determine whether the current contact pattern is changed from the first contact pattern to the second contact pattern.

That is, since L represents the number of confirmations of the second contact pattern, the L value greater than 0 means that the 2B-contact end 932 is out of contact with the tooth end 933B of the base cover 933.

When the first contact pattern is not changed from the first contact pattern to the second contact pattern and continues to be maintained, that is, when the L value is 0, step 1641 is performed.

In the step 1620, since the first contact pattern is still maintained after the driving module 300 is driven and the teeth of the driving wheel 420 of the driving unit 400 move once, when the control module 16 applies current to the encoder unit 930, the high signal is received.

In the step 1641, the control module 16 may increase the number of confirmations of the first contact pattern, that is, the H value by 1 in response to receiving the high signal. The control module 16 maintains the L value as 0.

After the step 1641, it returns to the step 1620 again.

Meanwhile, when the current contact pattern is changed from the first contact pattern to the second contact pattern, the process proceeds from the step 1640 to step 1642.

In the step 1642, the control module 16 may substitute the H value, which is the number of confirmations of the first contact pattern, into the C value, which is the evaluation value used to determine the over-injection or the under-injection.

The control module 16 may determine the over-injection or the under-injection based on the C value. For example, if the teeth of the driving wheel 420 move 100 times to make one rotation of the driving wheel 420 and the contact pattern changes eight times when the driving wheel 420 rotates one rotation, one contact pattern corresponds to 12.5 tooth movements. If the C value exceeds 13 times, the control module 16 may determine that the medical liquid is under-injected. Alternatively, if the C value is less than 12 times, the control module 16 may determine that the medical liquid is over-injected.

Although not illustrated in FIG. 16, when the over-injection or the under-injection is determined, the control module 16 may stop the operation of the medical liquid injection device 10 or induce the user to stop the operation of the medical liquid injection device 10 by notifying a notification.

If it does not correspond to the over-injection and the under-injection, step 1643 is performed.

In the step 1643, the control module 16 may reset the H value, which is the number of confirmations of the first contact pattern, to 0 and set the L value, which is the number of confirmations of the second contact pattern, to 1.

After the step 1643, the step 1620 is performed again.

When the step 1630 is performed again, the step 1650 is performed when the current contact pattern is the second contact pattern.

In the step 1650, the control module 16 may determine whether the current contact pattern is changed from the second contact pattern to the first contact pattern.

That is, since H represents the number of confirmations of the first contact pattern, the H value greater than 0 means that the 2B-contact end 932 is in contact with the tooth end 933B of the base cover 933.

When the first contact pattern is changed to the second contact pattern, that is, when the H value is 0, step 1651 is performed.

In the step 1620, since the second contact pattern is still maintained after the driving module 300 is driven and the teeth of the driving wheel 420 move once, when the control module 16 applies current to the encoder unit 930, the low signal is received.

In the step 1651, the control module 16 may increase the number of confirmations of the second contact pattern, that is, the L value by 1 in response to receiving the low signal. The control module 16 maintains the H value at 0.

After the step 1651, the step 1620 is performed again.

Meanwhile, when the current contact pattern is changed from the second contact pattern to the first contact pattern, the process proceeds from the step 1650 to step 1652.

In the step 1652, the control module 16 may substitute the L value, which is the number of confirmations of the second contact pattern, into the C value, which is the evaluation value used to determine the over-injection or the under-injection.

The control module 16 may determine the over-injection or the under-injection based on the C value. Using the example in the description of the step 1642 again, if the C value exceeds 13 times, the control module 16 may determine that the medical liquid is under-injected. Alternatively, if the C value is less than 12 times, the control module 16 may determine that the medical liquid is over-injected.

Although not illustrated in FIG. 16, when the over-injection or the under-injection is determined, the control module 16 may stop the operation of the medical liquid injection device 10 or induce the user to stop the operation of the medical liquid injection device 10 by notifying a notification.

If it does not correspond to the over-injection and the under-injection, step 1653 is performed.

In the step 1653, the control module 16 may reset the L value, which is the number of confirmations of the second contact pattern, to 0 and set the H value, which is the number of confirmations of the first contact pattern, to 1.

After the step 1653, the step 1620 is performed again.

Figure 17:
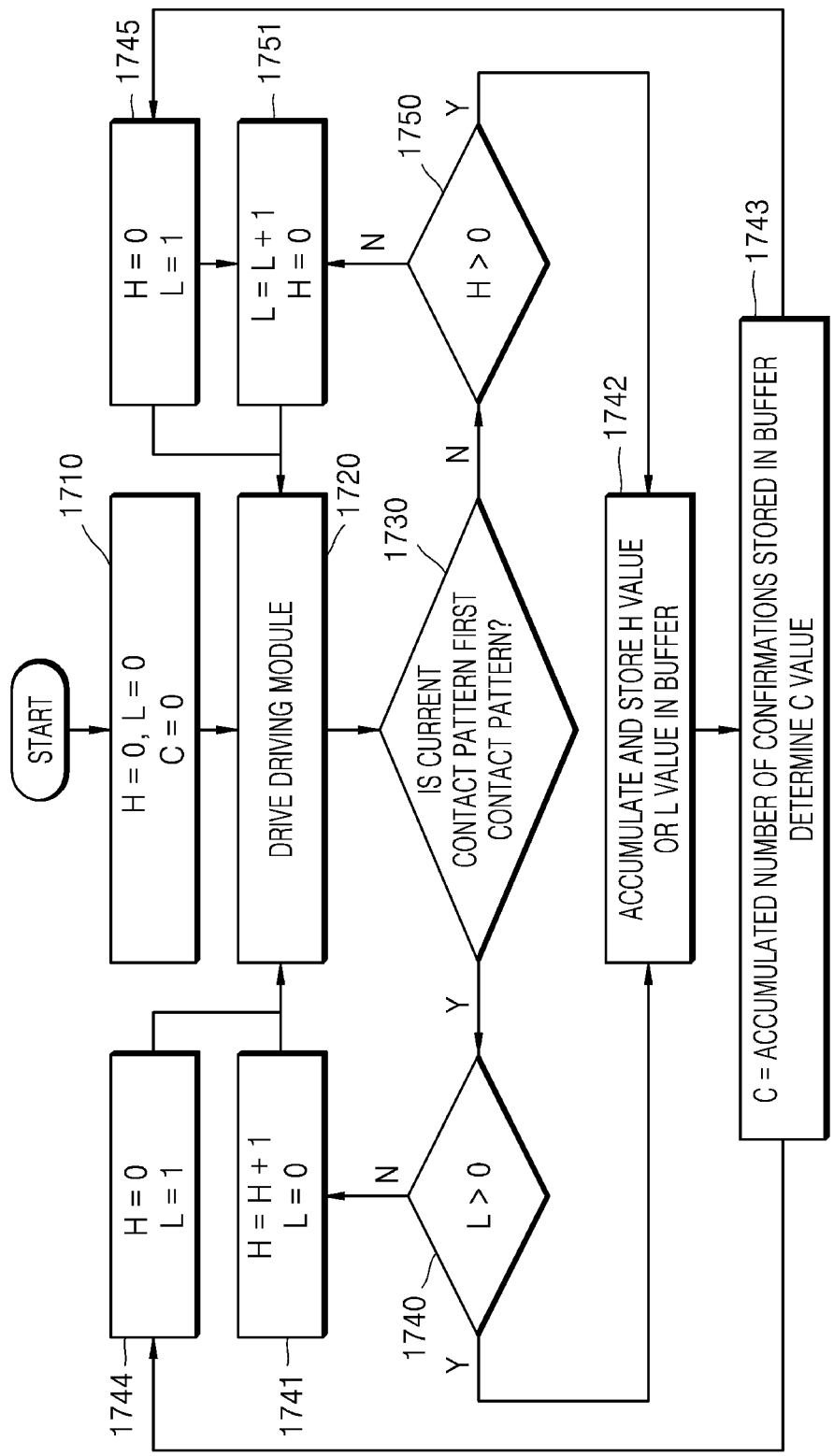
FIG. 17 is a flowchart illustrating a method of determining over-injection or under-injection of the medical liquid when a driving wheel according to an exemplary embodiment rotates once.

FIG. 17 is a flowchart illustrating a method of determining over-injection or under-injection of the medical liquid when a driving wheel according to an exemplary embodiment rotates once.

Descriptions of steps 1710, 1720, 1730, 1740, 1741, 1750 and 1751 of FIG. 17 are omitted because they overlap with those of the steps 1610, 1620, 1630, 1640, 1641, 1650 and 1651 of FIG. 16.

When the current contact pattern is the first contact pattern, in the step 1740, the control module 16 may determine whether the current contact pattern is changed from the first contact pattern to the second contact pattern.

When the current contact pattern is changed from the first contact pattern to the second contact pattern, the process proceeds from the step 1740 to step 1742.

In the step 1742, the control module 16 may the H value, which is store the number of confirmations of the first contact pattern, which is the contact pattern before changing, in a buffer.

Alternatively, when the current contact pattern is the second contact pattern, in the step 1740, the control module 16 may determine whether the current contact pattern is changed from the second contact pattern to the first contact pattern.

When the current contact pattern is changed from the second contact pattern to the first contact pattern, the process proceeds from the step 1750 to the step 1742.

In the step 1742, the control module 16 may store the L value, which is the number of confirmations of the second contact pattern, which is the contact pattern before changing, in the buffer.

The control module 16 may accumulate and store the number of confirmations of the contact pattern before changing in the buffer until the number of changes of the contact pattern becomes equal to or greater than a preset number.

For example, the preset number may be the number of times the contact pattern is changed while the driving wheel 420 rotates once. Specifically, in order for the driving wheel 420 to rotate one turn, the teeth of the driving wheel 420 may move 100 times, and the protruding end 420P and the tooth end 933B may be alternately positioned around the driving wheel 420 by four. In this case, when the driving wheel 420 rotates once, the contact pattern is changed eight times. In this case, the preset number may be 8 times.

When the number of changes of the contact pattern is equal to or greater than the preset number, step 1743 is performed.

In the step 1743, the control module 16 may substitute an accumulated number of confirmations stored in the buffer into the C value, which is the evaluation value used to determine the over-injection or the under-injection.

The control module 16 may determine the over-injection or the under-injection based on the C value. In the above example, when the C value is 101 times or more, the control module 16 may determine that the medical liquid is under-injected. Alternatively, if the C value is 99 times or less, the control module 16 may determine that the medical liquid is over-injected.

Although not illustrated in FIG. 17, when the over-injection or the under-injection is determined, the control module 16 may stop the operation of the medical liquid injection device 10, or may induce the user to stop the operation of the medical liquid injection device 10 by notifying a notification.

If it does not correspond to the over-injection and the under-injection, step 1744 or step 1745 is performed. The step 1744 may be performed when the current contact pattern is the first contact pattern, and the step 1745 may be performed when the current contact pattern is the second contact pattern.

In the step 1744, the control module 16 may reset the H value, which is the number of confirmations of the first contact pattern, to 0 and set the L value, which is the number of confirmations of the second contact pattern, to 1.

In the step 1745, the control module 16 may reset the L value, which is the number of confirmations of the first contact pattern, to 0 and set the H value, which is the number of confirmations of the second contact pattern, to 1.

After the steps 1744 and 1745, the step 1720 is performed again.

Meanwhile, the control module 16 may apply different methods for determining each of the under-injection and the over-injection.

For example, the control module 16 may determine under-injection of the medical liquid whenever the driving module 300 is driven and the teeth of the driving wheel 420 of the driving unit 400 move once. That is, the control module 16 may determine the under-injection of the medical liquid whenever the contact pattern is checked. In addition, the control module 16 may determine the over-injection of the medical liquid whenever the driving wheel 420 rotates once.

Specifically, the control module 16 may determine that the current contact pattern for the encoder unit 930 is the first contact pattern or the second contact pattern.

The control module 16 may check whether the current contact pattern remains the first contact pattern or the second contact pattern and calculate the number of confirmations.

The control module 16 may store the number of confirmations of the contact pattern before changing in the buffer in response to the change of the current contact pattern from the first contact pattern to the second contact pattern or from the second contact pattern to the first contact pattern.

The control module 16 may accumulate and store the number of confirmations in the buffer until the number of changes of the contact pattern exceeds the preset number. The control module 16 may determine the over-injection of the medical liquid based on the accumulated number of confirmations stored in the buffer in response to the number of changes of the contact pattern being equal to or greater than the preset number.

The control module 16 may determine whether to over-inject the medical liquid based on the accumulated number of confirmations stored in the buffer whenever the driving wheel 420 rotates once. The control module 16 may substitute the accumulated number of confirmations into a second evaluation value (C2 value) and determine whether to over-inject the medical liquid based on the C2 value.

For example, the preset number may be the number of times the contact pattern is changed while the driving wheel 420 rotates once. Specifically, in order for the driving wheel 420 to rotate one turn, the teeth of the driving wheel 420 may move 100 times, and the protruding end 420P and the tooth end 933B may be alternately positioned around the driving wheel 420 by four. In this case, when the driving wheel 420 rotates once, the contact pattern is changed eight times. In this case, the preset number may be 8 times. If the C2 value is 99 times or less, the control module 16 may determine that the medical liquid is over-injected. At this time, if the C2 value is 101 times or more, the control module 16 may determine that the medical liquid is under-injected. Alternatively, the determination of the case where the C2 value is 101 times or more may be omitted.

In addition, the control module 16 may determine whether the medical liquid is under-injected, based on a sum of the accumulated number of confirmations accumulated in the buffer when the number of changes of the contact pattern is 'preset number–1' and the number of confirmations of the current contact pattern. The control module 16 substitutes the number of sum into a first evaluation value (C1 value), and may determine whether the medical liquid is under-injected based on the C1 value.

For example, if the teeth of the driving wheel 420 move 100 times to make one rotation of the driving wheel 420 and the contact pattern changes eight times when the driving wheel 420 rotates one rotation, one contact pattern corresponds to 12.5 tooth movements. In this case, the preset number may be 8 times, and 'preset number–1' may be 7 times. The control module 16 may determine the under-injection of the medical liquid, based on the sum of the accumulated number of confirmations stored in the buffer while the contact pattern is changed 7 times and the number of confirmations for the current contact pattern.

Specifically, since one contact pattern corresponds to 12.5 tooth movements, the tooth may move 87.5 times on average while the contact pattern is changed 7 times. That is, if the first decimal place is rounded up or down, the C1 value may be '87 times+number of confirmations for current contact pattern' or '88 times+number of confirmations for current contact pattern'. Since the teeth of the driving wheel 420 need to move 100 times in order for the driving wheel 420 to rotate one revolution, when the C1 value is 101 times or more, the control module 16 may determine that the medical liquid is under-injected. At this time, the judgment for the case where the C1 value is 99 times or less may be omitted.

The movement of the teeth of the driving wheel 420 is delayed when the medical liquid is under-injected, so the under-injection may be recognized late when determining whether the medical liquid is under-injected based on when the driving wheel 420 rotates once or when the contact pattern is changed. In addition, when the movement of the teeth of the driving wheel 420 is stopped, a situation where it is not possible to determine the under-injection may occur. Considering this point, in the present disclosure, whether the medical liquid is under-injected is determined every time the contact pattern is checked, and whether the medical liquid is over-injected is determined every time the driving wheel 420 rotates one turn, thereby solving all the problems described above.

Various embodiments of the present disclosure may be implemented in software (e.g., program) including one or more instructions stored in a machine-readable storage medium. For example, a processor of the machine may call at least one of the stored one or more instructions from the storage medium and execute it. This enables the machine to be operated to perform at least one function according to the called one or more instructions. The one or more instructions may include code generated by a compiler or code executable by an interpreter. A machine-readable storage medium may be provided in a form of a non-transitory storage medium. Here, 'non-temporary' only means that the storage medium is a tangible device and does not contain a signal (e.g., electromagnetic wave), and this term does not distinguish between a case in which data is semi-permanently stored in the storage medium and a case in which data is temporary stored.

According to one embodiment, the method according to various embodiments of the present disclosure may be included and provided in a computer program product. The computer program product may be traded between a seller and a buyer as a commodity. The computer program product may be distributed in a form of the machine-readable storage medium (e.g., compact disc read only memory (CD-ROM)), or may be distributed (i.e. downloaded or uploaded) directly or online between two user devices through an application store (e.g., Play Store™). In the case of online distribution, at least part of the computer program product may be temporarily stored or temporarily generated in the machine-readable storage medium such as a manufacturer' server, an application store server, or a relay server's memory.

Also, in this specification, "unit" may be a hardware component such as a processor or a circuit, and/or a software component executed by the hardware component such as a processor.

The scope of the present embodiment is indicated by the claims to be described later rather than the detailed description above, and should be construed as including all changes or modifications derived from the meaning and scope of the claims and equivalent concepts thereof.

According to one embodiment of the present disclosure, a medical liquid injection device may be applied to various industrially available devices. The medical liquid injection device may be applied to devices for delivering various medical liquids.

What is claimed is:

1. A medical liquid injection device comprising:
   a base body;
   a needle assembly mounted on the base body;
   a reservoir fluidly connected to the needle assembly and having a plunger therein;
   a driving unit that linearly moves the plunger; and
   an encoder unit disposed at an end of the driving unit to measure rotation of the driving unit, wherein
   the encoder unit comprises:
   a base cover mounted on the end of the driving unit and rotating together with the driving unit;
   a first contact end connected to contact one side of the base cover; and
   a second contact end disposed on another side of the base cover and selectively contacting the base cover according to rotation of the driving unit,
   the base cover comprises:
   a cover end extending in a circumferential direction of the driving unit which rotates; and
   a plurality of tooth ends extending from the cover end and spaced apart from each other along the circumferential direction of the cover end,
   the driving unit comprises:
   a protruding end disposed between adjacent tooth ends of the plurality of tooth ends, and a height of the protruding end varies in a radial direction thereof so that the protruding end and the tooth ends have a step in a circumferential direction, and
   the protruding end has a first wall and a second wall on one side and another side thereof, respectively, wherein a height of the first wall is smaller than a height of each of the tooth ends and the height of the second wall is greater than the height of the tooth end, and a height of the protruding end is increased from the first wall to the second wall.

2. The medical liquid injection device of claim 1, wherein the first contact end and the second contact end each have elasticity.

* * * * *